US010758717B2

(12) United States Patent
Gianotti et al.

(10) Patent No.: US 10,758,717 B2
(45) Date of Patent: *Sep. 1, 2020

(54) MECHANICALLY ACTUATED AND FUNCTIONALLY INTEGRATABLE CATHETER SYSTEM FOR TREATING VASCULAR AND NON-VASCULAR DISEASES AND RELATED METHODS

(71) Applicant: CTI Vascular AG, Neuhausen (CH)

(72) Inventors: Marc Gianotti, Wiesendangen (CH); Ulf Fritz, Tengen (DE); Dragana Gajic, Schaffhausen (CH)

(73) Assignee: CTI Vascular AG, Neuhausen (CH)

( * ) Notice: Subject to any disclaimer, the term of this patent is extended or adjusted under 35 U.S.C. 154(b) by 297 days.

This patent is subject to a terminal disclaimer.

(21) Appl. No.: 15/744,027

(22) PCT Filed: Jan. 11, 2016

(86) PCT No.: PCT/EP2016/050375
§ 371 (c)(1),
(2) Date: Jan. 11, 2018

(87) PCT Pub. No.: WO2017/008917
PCT Pub. Date: Jan. 19, 2017

(65) Prior Publication Data
US 2018/0200490 A1 Jul. 19, 2018

Related U.S. Application Data

(60) Provisional application No. 62/191,517, filed on Jul. 13, 2015.

(51) Int. Cl.
A61M 25/10 (2013.01)
A61M 25/00 (2006.01)
(Continued)

(52) U.S. Cl.
CPC ...... *A61M 25/104* (2013.01); *A61M 25/0097* (2013.01); *A61M 25/0113* (2013.01);
(Continued)

(58) Field of Classification Search
CPC ...... A61M 2025/0681; A61M 25/0097; A61M 2025/0004; A61M 2025/1052;
(Continued)

(56) References Cited

U.S. PATENT DOCUMENTS 4,323,071 A * 4/1982 Simpson ........... A61M 25/0054
128/DIG. 18

* cited by examiner

Primary Examiner — Katherine M Shi

(57) ABSTRACT

A comprehensive multi-functional device platform that can be variably configured by clinician operators for patient-specific anatomies and clinical situations for treating complex and total occlusions is provided. This device platform enables physicians of any skill level to effectively treat the most challenging and complex lesions/occlusions more conveniently in less time. The Functionally Integratable Catheter System ("FICS System") represents a system of "functional units" that can be configured together to operate synergistically, and comprises at least four main "functional units," including: (a) FICS Support Catheter; (b) FICS Dilator; (c) FICS PTA Catheter; and (d) FICS Lock-Grip Handle. Each "functional unit" can be provided in a pre-assembled form by the manufacturer, intended to be configured into variable combinations by clinician operators.

20 Claims, 15 Drawing Sheets

(51) Int. Cl.
*A61M 29/02* (2006.01)
*A61M 29/00* (2006.01)
*A61M 25/01* (2006.01)
*A61M 25/06* (2006.01)

(52) U.S. Cl.
CPC ............ *A61M 29/00* (2013.01); *A61M 29/02* (2013.01); *A61M 25/0136* (2013.01); *A61M 2025/0004* (2013.01); *A61M 2025/0681* (2013.01); *A61M 2025/1068* (2013.01)

(58) Field of Classification Search
CPC ............ A61M 25/0136; A61M 25/104; A61M 2025/09175; A61M 2025/09183; A61M 2025/1047; A61M 25/10; A61M 25/1011; A61M 25/1018; A61M 29/00; A61B 2017/22048; A61B 2017/2206; A61B 2017/22051
See application file for complete search history.

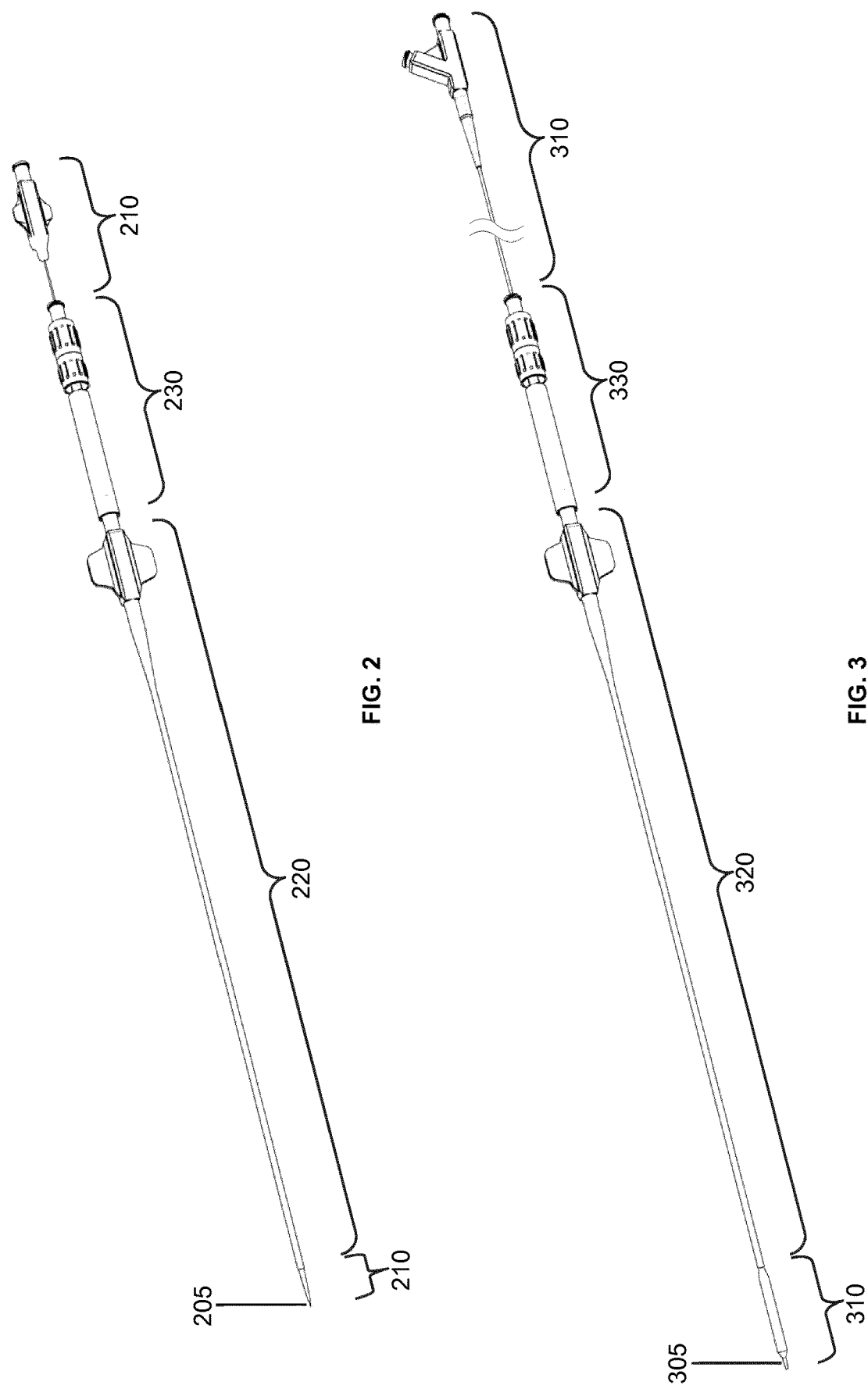

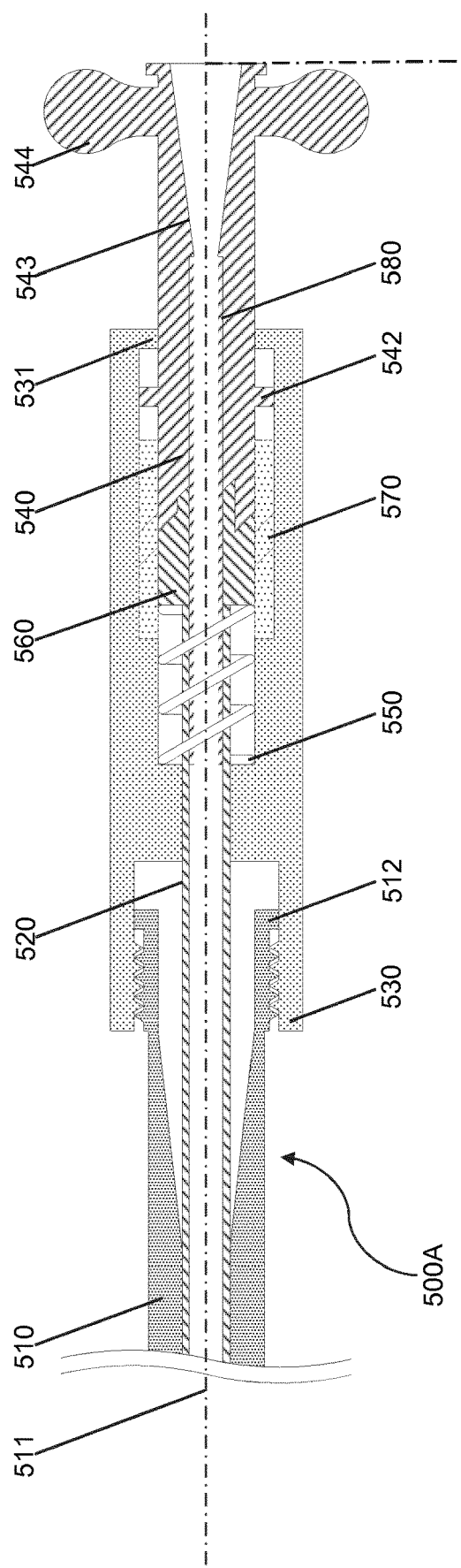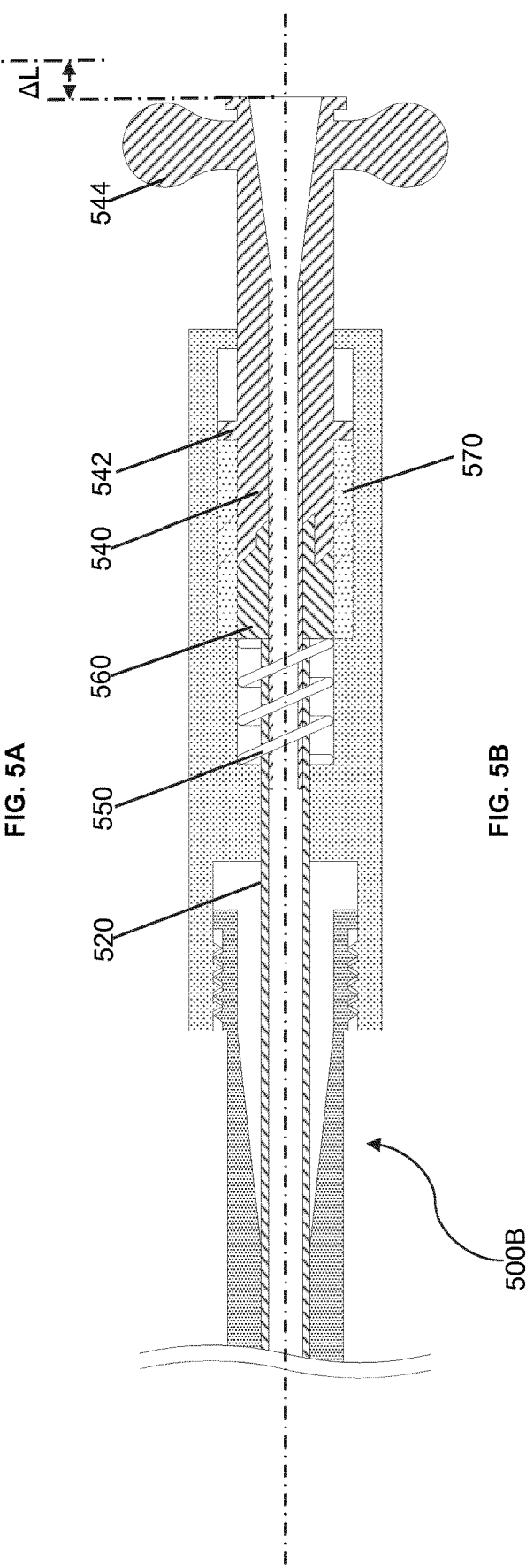
FIG. 5A
FIG. 5B

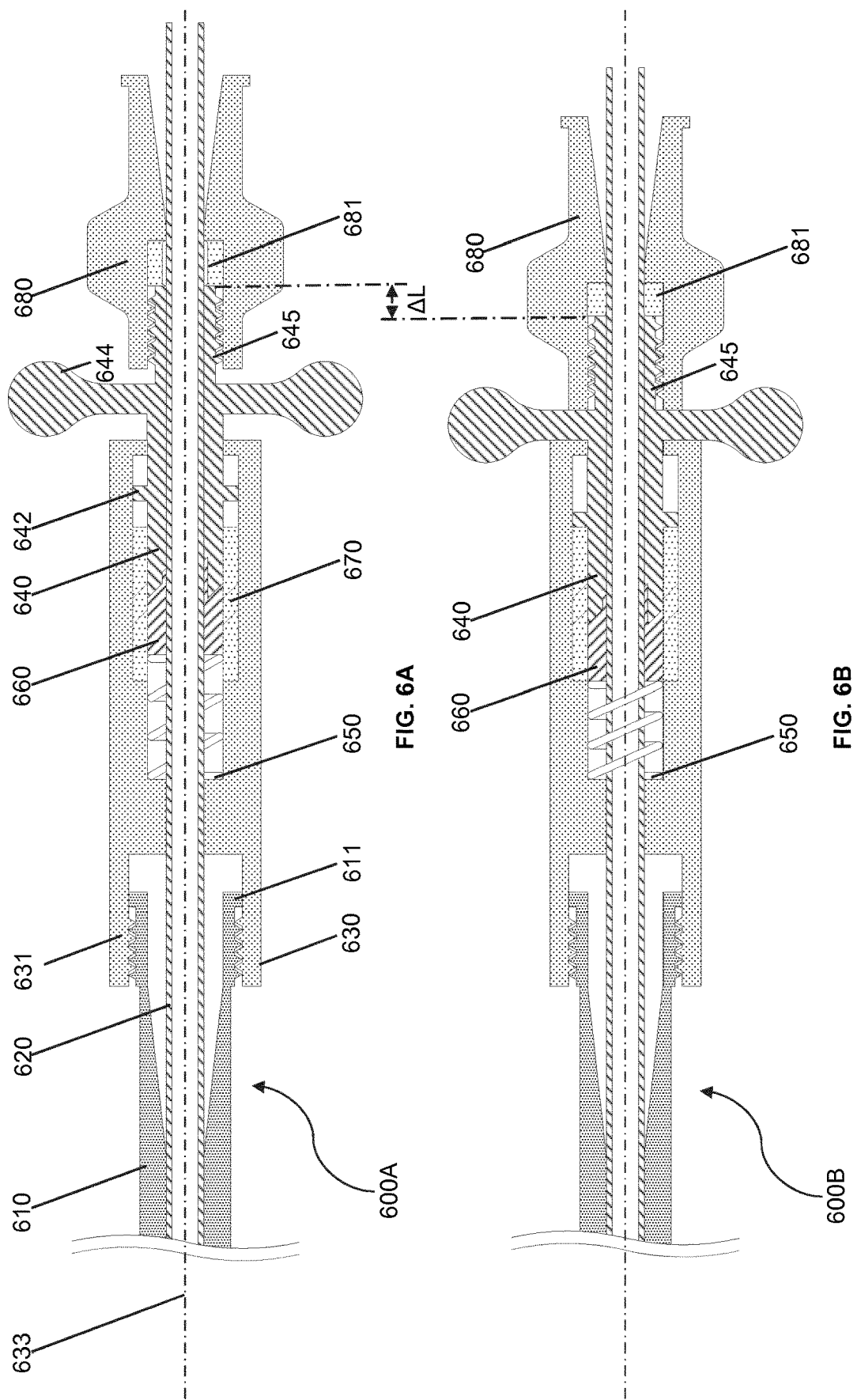

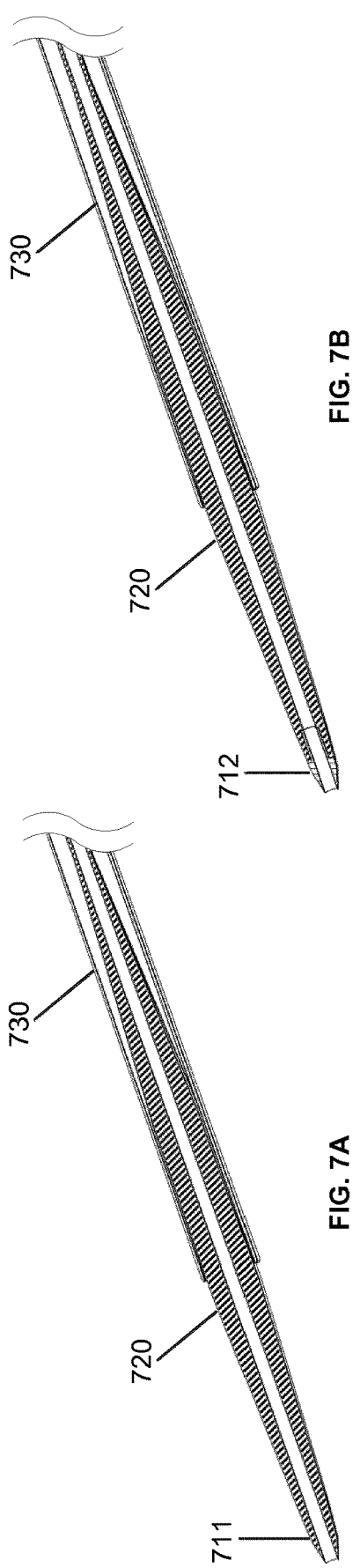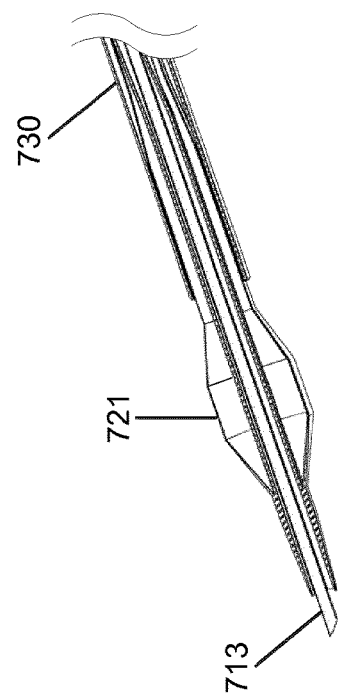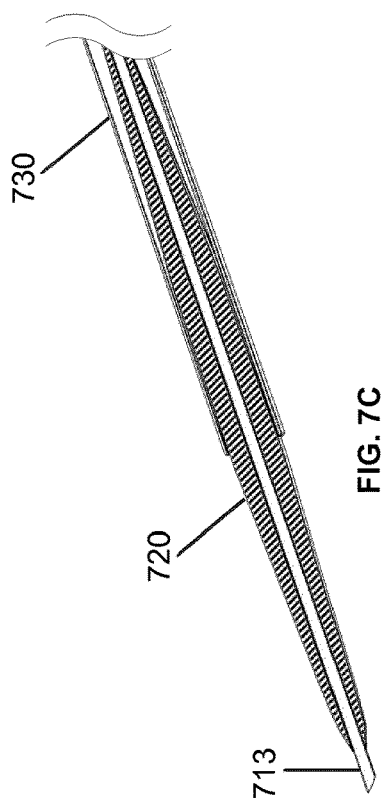
FIG. 7A
FIG. 7B
FIG. 7C
FIG. 7D
FIG. 7

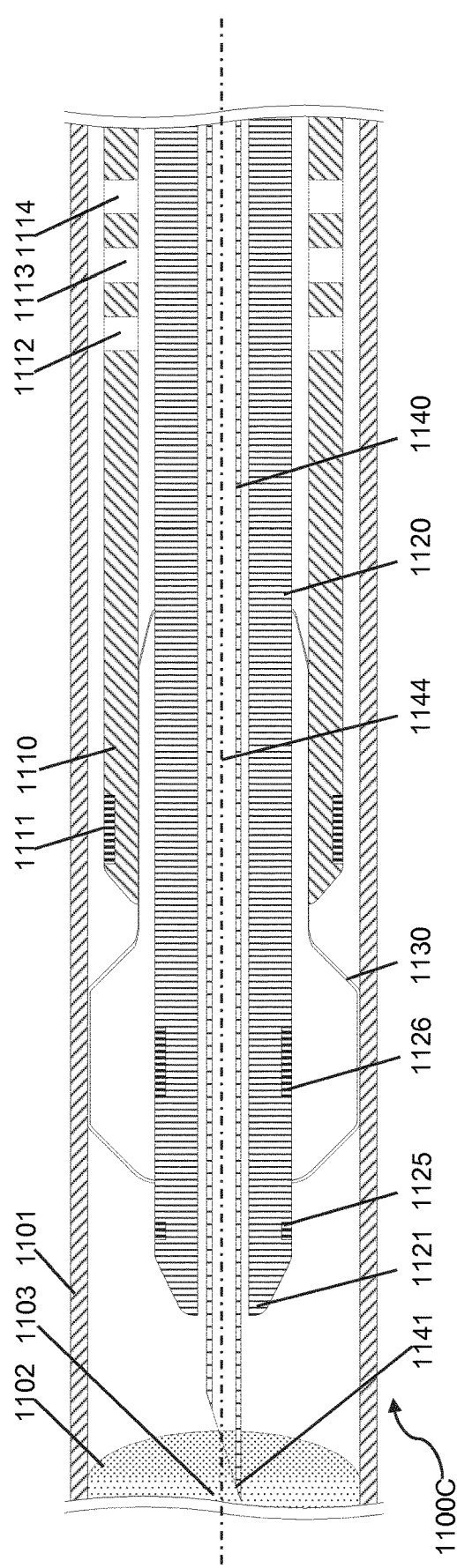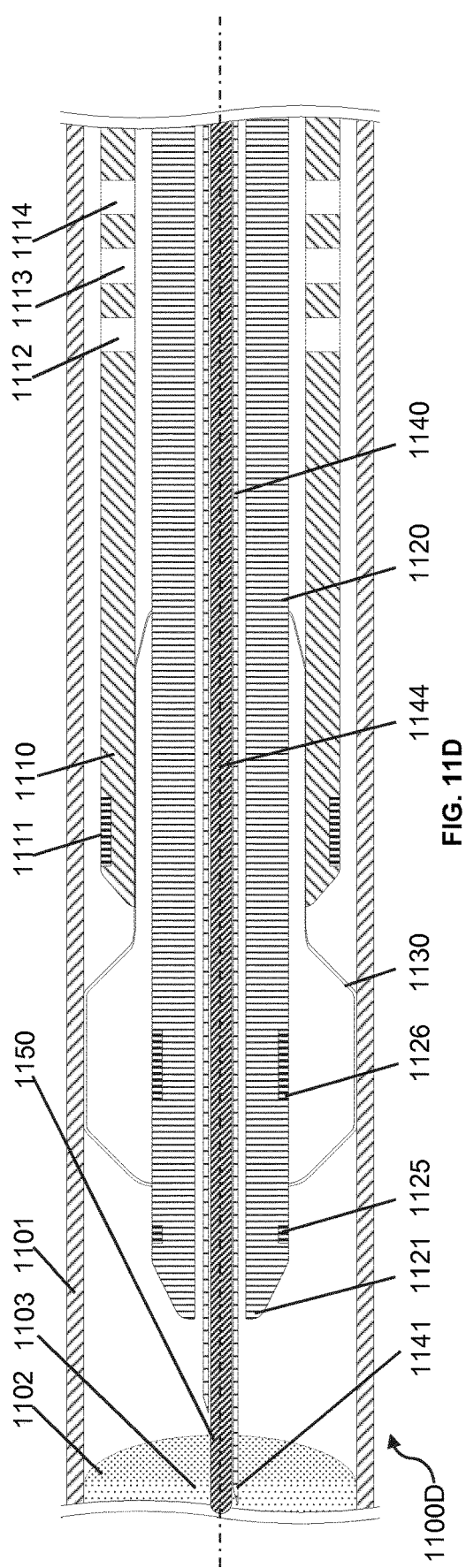
FIG. 11C
FIG. 11D

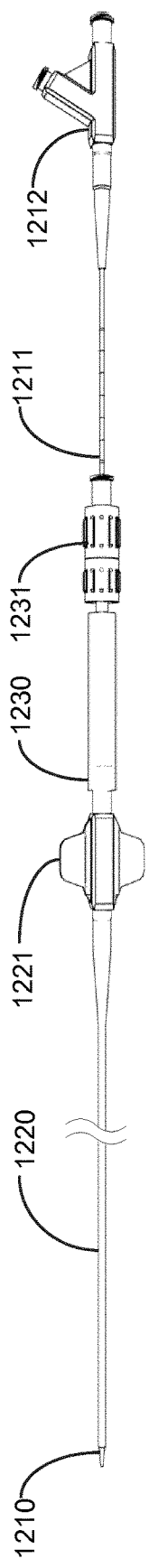 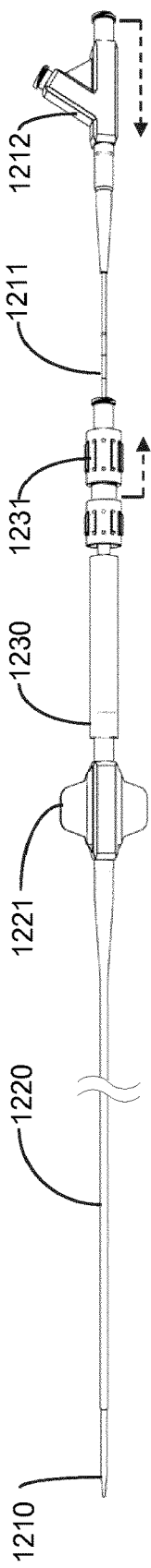 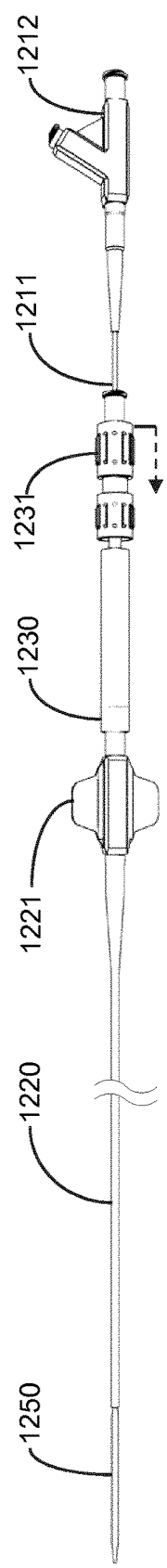 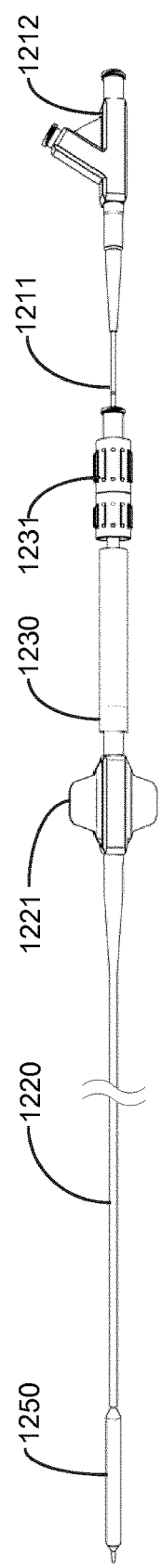
FIG. 12

MECHANICALLY ACTUATED AND FUNCTIONALLY INTEGRATABLE CATHETER SYSTEM FOR TREATING VASCULAR AND NON-VASCULAR DISEASES AND RELATED METHODS

CROSS-REFERENCE TO RELATED APPLICATIONS

This application claims priority to PCT Application No. PCT/EP2016/050375, filed Jan. 11, 2016, which claims the benefit of U.S. provisional application 62/191,517, filed on Jul. 13, 2015, the content of which is hereby incorporated by reference in entirety.

TECHNICAL FIELD

The present disclosure is related to a mechanically enabled functionally integratable catheter system ("FICS System"), comprising a support catheter, a dilator, a balloon catheter and a lock-grip handle, which can be functionally and dimensionally configured for their in vivo assembly, in various configurations, by physicians, for the treatment of vascular and non-vascular conditions/diseases, including complex lesions and chronic total occlusions (CTO).

BACKGROUND OF THE INVENTION

Atherosclerosis is a specific type of vascular disease, manifested by the accumulation of degenerative material along the lumen of blood vessel walls. Atherosclerosis is acknowledged as one of the major leading causes of death and morbidity in the Western world. Atherosclerosis can be asymptomatical at the early stages without noticeable discomfort or pain. However, if the disease progresses unabated, the affected vessels can develop plaques exhibiting variable textures resulting in increasingly complex lesion(s), for which the size and the severity can cause (a) successive reduction in lumen diameter; (b) restriction in blood flow; and (c) impairment in vessel flexibility in direct response to substantial thickening and hardening of blood vessels attributed to the cumulative formation of plaques/lesions along affected vessels. A chronic plaque build-up (i.e., composed of mixtures of fatty, fibrous and/or calcified tissue matters) can eventually reach a state, where blood flow becomes entirely insufficient to support the perfusion of local tissues, leading to a condition known as "chronic total occlusion" (CTO). CTO recanalization treatments to re-open obstructed vessels can present a number of inherent technical challenges to engineers who design medical devices that enable CTO recanalization and to physicians who depend on the use of clinically approved medical devices provided by device manufacturers. Ideally, the practicing physicians would have access to the most effective therapeutic medical devices in order to penetrate inherently challenging CTO situations of any size and severity, regardless of patient-specific anatomical variations. Currently, the interventional instruments available for physicians may be adequate; however, some procedural inefficiencies and limitations continue to exist due to the inherent limitations in product design and patient anatomical complexities. There is an unmet need to provide improved medical devices for treating complex lesions and chronic total occlusions (CTO) caused by atherosclerotic diseases.

SUMMARY

The present disclosure provides a comprehensive multi-functional device platform for treating complex lesions, including total occlusions, enabling physicians of any skill level to effectively treat the most challenging and complex vessel pathologies more conveniently in less time. The present disclosure provides a Functionally Integratable Catheter System ("FICS") representing a system of "functional units" that can be assembled by clinical operators, as therapeutic-specific "configurations" that can operate synergistically. FICS comprises at least four main "functional units," including: (a) FICS Support Catheter; (b) FICS Dilator; (c) FICS PTA Catheter; and (d) FICS Lock-Grip Handle. Each "functional unit" can be provided in a pre-assembled form by the manufacturer, optionally pre-packaged as a device tray that includes the functional units (a)-(d), intended to be selectively assembled into variable configurations by clinical operators. The configurational adaptability of the FICS platform enables the physician to efficiently address multiple procedural aspects of the clinical intervention process (e.g., lesion access, lesion penetration, guide wire negotiation, lesion recanalization and dilation) by providing in situ treatment options (intraluminal and/or extraluminal recanalization), and enables multi-stage, patient-customized treatments of complex lesions in vivo (lesion-length-selective, multi-stage angioplasty treatment). In particular, the FICS System can be selectively configured by a clinical operator in order to recanalize extended complex lesions by providing a length-adaptable balloon member capable of matching the length of a target lesion ("lesion-length adjustability") conferred by the "FICS LLS PTA configuration" disclosed herein. A visual map of the various "functional units" and "functional subunits" that can be selectively combined by a clinical operator for constructing specific "FICS configurations" most effective for treating a broad range of complex lesions and CTOs is provided in a flow-chart diagram in FIG. 15.

Various embodiments are directed to the FICS components that can be pre-assembled into various "functional units" by the manufacturer. Various embodiments are directed to the specific "configurations" that can be assembled together by clinical operators involving the selective combination of different FICS "functional units" that can be configured specifically to be most effective in treating a broad range of complex lesions and CTOs. Various embodiments are directed to methods for manufacturing the FICS "functional units" and "functional subunits" disclosed herein. Various embodiments are directed to the methods for treating vascular and/or non-vascular diseases utilizing one or more disclosed "FICS configurations" for facilitating several therapeutic functionalities, including improved: (a) guide-wire negotiations; (b) lesion penetrations; (c) lesion recanalizations; (d) lesion dilations; and (e) vessel-lumen restorations.

BRIEF DESCRIPTION OF THE DRAWINGS

FIG. 2 illustrates the assembled "FICS Dilator configuration" adaptable for intraluminal and/or extraluminal recanalization, as an embodiment.

FIG. 3 illustrates the assembled "FICS LLS PTA Catheter configuration" useful for lesion-length selectivity, as an embodiment.

FIGS. 5 A-B illustrate cross-lateral views of a "dilator-tip propagation mechanism" (Style A) connected to the proximal end of the FICS Support Catheter, as one embodiment.

FIGS. 6 A-B illustrate cross-lateral views of a "dilator-tip propagation mechanism" (Style B) connected to the proximal end of the FICS Support Catheter, as one embodiment.

FIGS. 7 A-D illustrate cross-lateral views of four mechanically actuatable FICS Dilator Tip configurations, wherein FIG. 7A represents the "Basic Tip" style; FIG. 7B represents the "Reinforced Tip" style; FIG. 7C represents the "Basic & Hypotube" style; FIG. 7D represents the "LLS & Hypotube" style, as several embodiments.

FIG. 8 illustrates exemplary dilator tips for facilitating intraluminal and/or extraluminal recanalization.

FIGS. 12 A-D illustrate the inter-operability of the functional units for enabling in vivo "lesion-length selectivity" and deploying the FICS LLS PTA configuration in successive multi-level stages, as an embodiment.

DETAILED DESCRIPTION

A. Definitions

The term "a" refers to one or more modified nouns and/or pronouns.

The term "Functionally Integratable Catheter System" ("FICS System") refers to various combinations of the disclosed "functional units," wherein each unique combination is referenced herein as therapeutic-specific "configurations." The FICS System comprises at least four main "functional units," including: (a) FICS Support Catheter; (b) FICS Dilator; (c) FICS PTA Catheter; and d) FICS Lock-Grip Handle. Each "functional unit" of the FICS System is further described in the following subsections, including figures, tables, and examples. FICS System enables continuous access to multiple number of lesions within an affected vessel by providing relative positional stabilization between the FICS Support Catheter and other "functional units" by maintaining the FICS Support Catheter in place, in contrast to conventional practices requiring the removal of generic support catheters and/or guidewires during therapeutic intervention. The cycle of dis-assembly and re-assembly may be repeated multiple times as necessary by clinical operators for treating an affected vessel in a continuous, multi-staged procedure.

The terms "configuration(s)" or "FICS configuration(s)" refer to therapeutic-specific combinations of the individual "functional units" that can be reversibly co-assembled, dis-assembled, and re-assembled by clinical operators (e.g., interventional physicians) to obtain multiple inter-operable devices (i.e., FICS System) suitable for treating any type of complex lesions/CTOs encountered during intervention. A visual map of the various "functional units" and "functional subunits" that can be selectively combined by a clinical operator for constructing specific "FICS configurations" most effective for treating a broad range of complex lesions and CTOs is referenced in FIG. 15.

Figure 15:
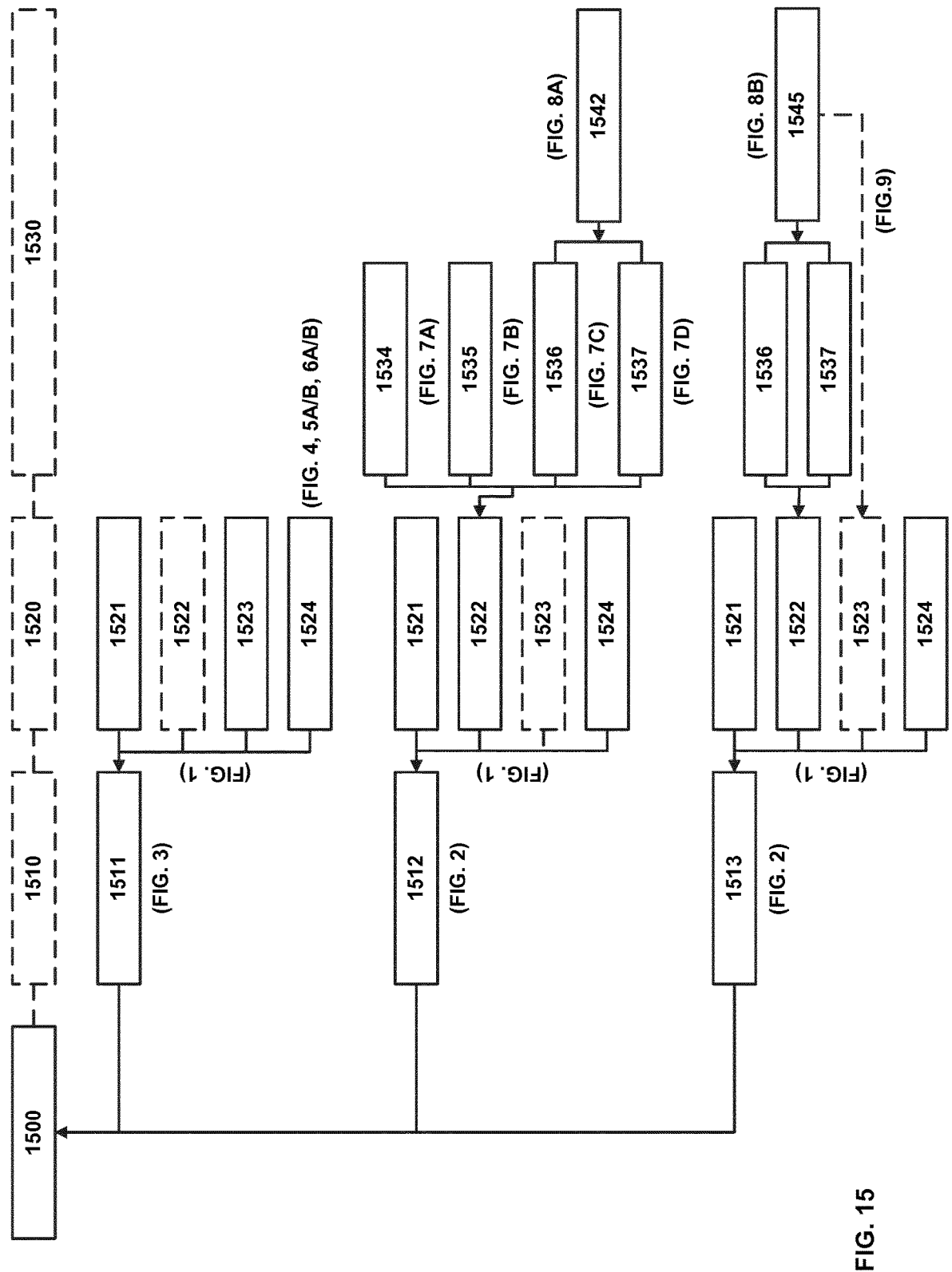
FIG. 15 is a flow-chart overview of the possible FICS System "configurations" as contemplated herein, providing a visual map of the various "functional units" and "functional subunits" that can be selectively combined by a clinical operator for constructing therapeutic-specific "configurations" most effective for treating a broad range of complex lesions and CTOs.

The term "functional subunits" refers to the "FICS subunits" that can be provided in pre-assembled states as optional configurational alternatives to enable/enhance a particular functionality of the highly adaptable FICS System by providing different therapeutic-specific "FICS configurations" as referenced in FIG. 15. In particular, several "design" options in constructing the various FICS Dilator tips (FIGS. 7 A-D) comprising "CTO Penetration Tip" (FIG. 8A), and "Reentry Tip" (FIG. 8B) for the distal tip portion of the mechanically actuated FICS Dilator are disclosed.

The term "pre-configured" refers to the state of a functional unit that is not assembled or configured together by a clinical operator to obtain one or more operable "FICS configurations" as referenced conveniently in FIG. 15.

The term "functionally integratable" refers to the capability of the "functional units" of the disclosed FICS System to be assembled together or interconnected into various therapeutic-specific "FICS configurations" having improved operational characteristics and benefits, as compared to the operational effectiveness of each pre-assembled functional unit. Each individual component may be operational in a pre-configured state, but having limited functionality as a standalone device, as compared to the enhanced performance characteristics expected of the dimensionally configured functional units (i.e., FICS configurations) represented in FIG. 15. As used herein, the functional combination (co-assembly/re-assembly) of the various "functional units" and "functional subunits" of the disclosed FICS System can be reversibly disassembled after use for a first medical procedure in preparation to be re-assembled into a different "FICS configuration" for use during a second subsequent medical procedure (e.g., for the treatment of a second lesion) in the same or different affected vessel.

The term "FICS Support Catheter" ("SC") refers to a stabilizing catheter positioned over a pre-disposed guide-wire ("GW") that can protect delicate vessels during an interventional procedure by providing a structurally guiding shield for maneuvering other FICS "functional units" through the lumen space. As a specific feature, the SC comprises a distal working end (the section of an instrument that is useful for performing certain therapeutic procedures) that can be variably adapted by the physician by physically supporting and guiding the insertion of other FICS "functional units" as necessary for comprehensively treating complex lesions, including total occlusions.

The term "FICS Dilator" refers a "functional unit" useful for dilating affected vessels by initially creating an opening and subsequently forming an entryway for other FICS functional units such as the FICS LLS PTA Catheter and guide wires. The FICS Dilator comprises a shaft having a distal tip portion that can be projected distally by a mechanically actuated spring mechanism. As a specific feature, the FICS Dilator has a distal working end that can be designed to incorporate specifically designed tips that can provide various functionalities for enabling intraluminal and/or extraluminal recanalization (FIGS. 7-8).

Figure 8B:
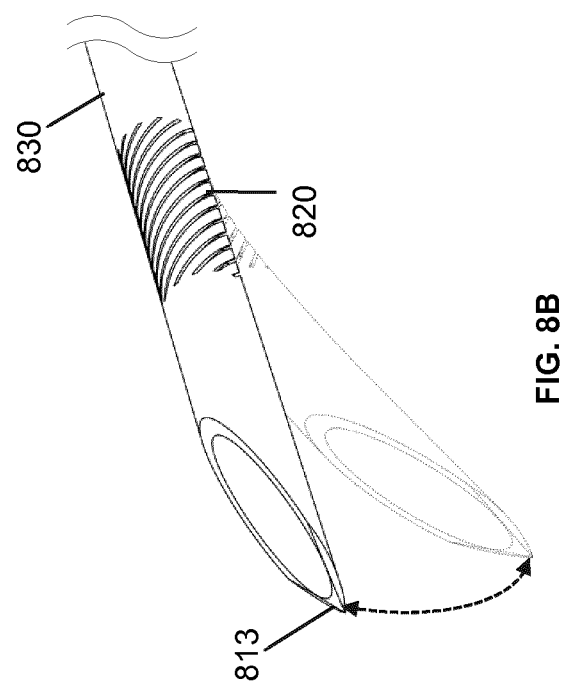
FIG. 8B is a magnified view of a "Reentry Tip" comprising a malleable and angled hypotube of the FICS Dilator, suitable for extraluminal recanalization, as an embodiment.
Figure 8A:
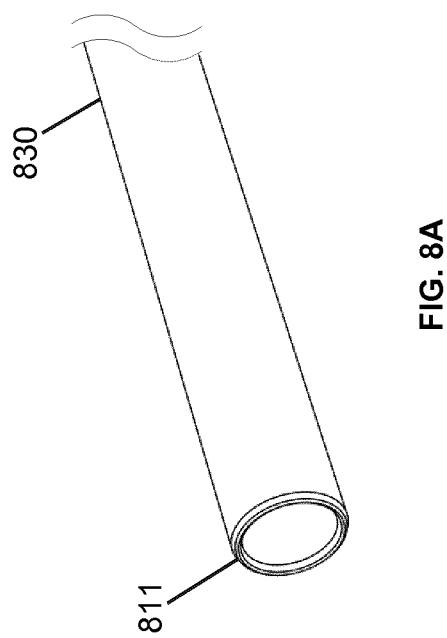
FIG. 8A is a magnified view of a "CTO Penetration Tip" comprising a non-malleable and blunt-ended hypotube of the FICS Dilator suitable for intraluminal recanalization, as an embodiment.

The term "FICS CTO Dilator" refers to a FICS configuration obtained by inserting the FICS Dilator incorporating a "CTO Penetration Tip" within the FICS Support Catheter intended for intraluminal recanalization (FIGS. 2 and 8A).

The term "FICS Reentry Dilator" refers to a FICS configuration obtained by inserting the FICS Dilator incorporating a "Reentry Tip" within the FICS Support Catheter intended for extraluminal recanalization (FIGS. 2 and 8B).

The term "CTO Penetration Tip" refers to various tip designs contemplated for constructing the dilator tip portions of the mechanically actuated FICS Dilator that can be specifically adapted to be suitable for effecting CTO penetrations, applicable to the therapeutic-specific "FICS configurations" referenced in FIG. 15 (FIGS. 7 A-D and 8A).

Figure 9:
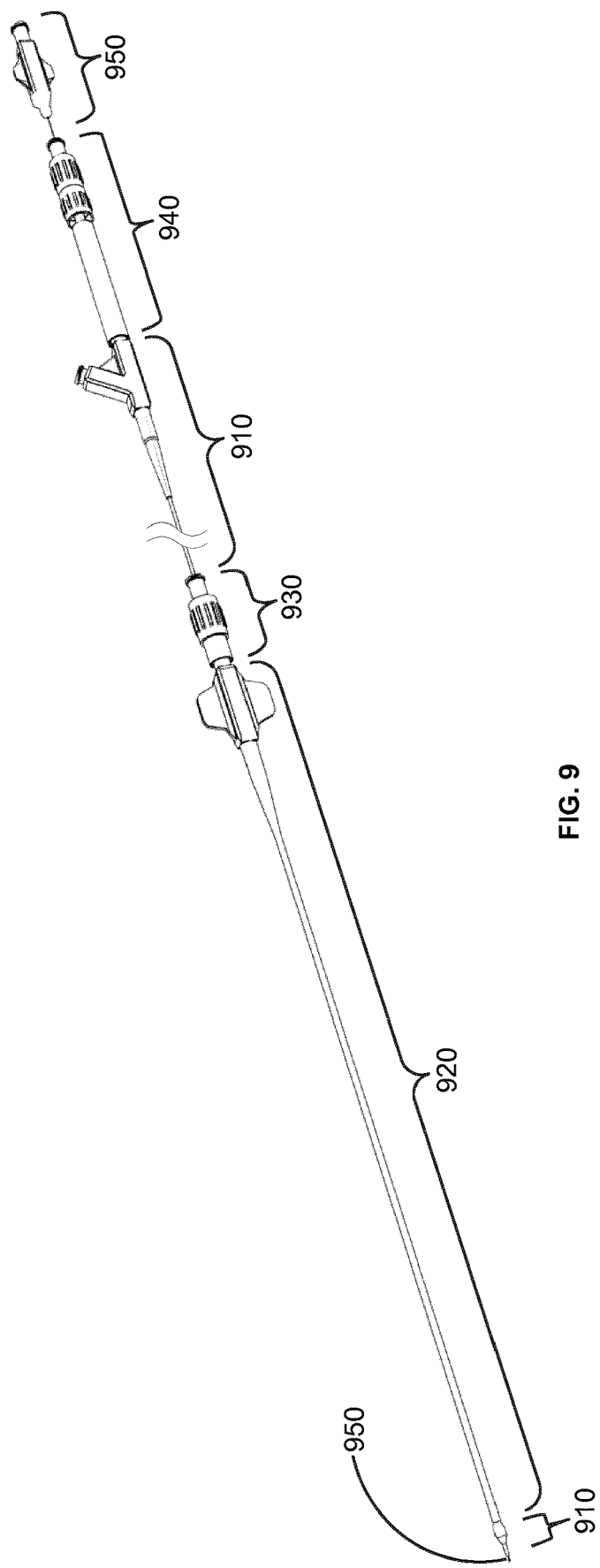
FIG. 9 illustrates a perspective view of the FICS Dilator assembled with the FICS PTA Catheter, forming a steerable "LLS & Hypotube" dilator tip, useful for "lesion-length selective" anchoring/centering, as an embodiment.

The term "Reentry Tip" refers to various tip designs contemplated for constructing the dilator tip portions of the mechanically actuated FICS Dilator that can be specifically adapted to be suitable for effecting subintimal access and reentry, applicable to the therapeutic-specific "FICS configurations" referenced in FIG. 15. The specialized FICS Reentry tip design is intended for enabling extraluminal recanalization and can be controllably diverted by incorporating a malleable tip segment (FIG. 8B). The "FICS Reentry Tip" can be most effective when combined with a torque-stable, steerable FICS Dilator (FIG. 9).

Figure 4:
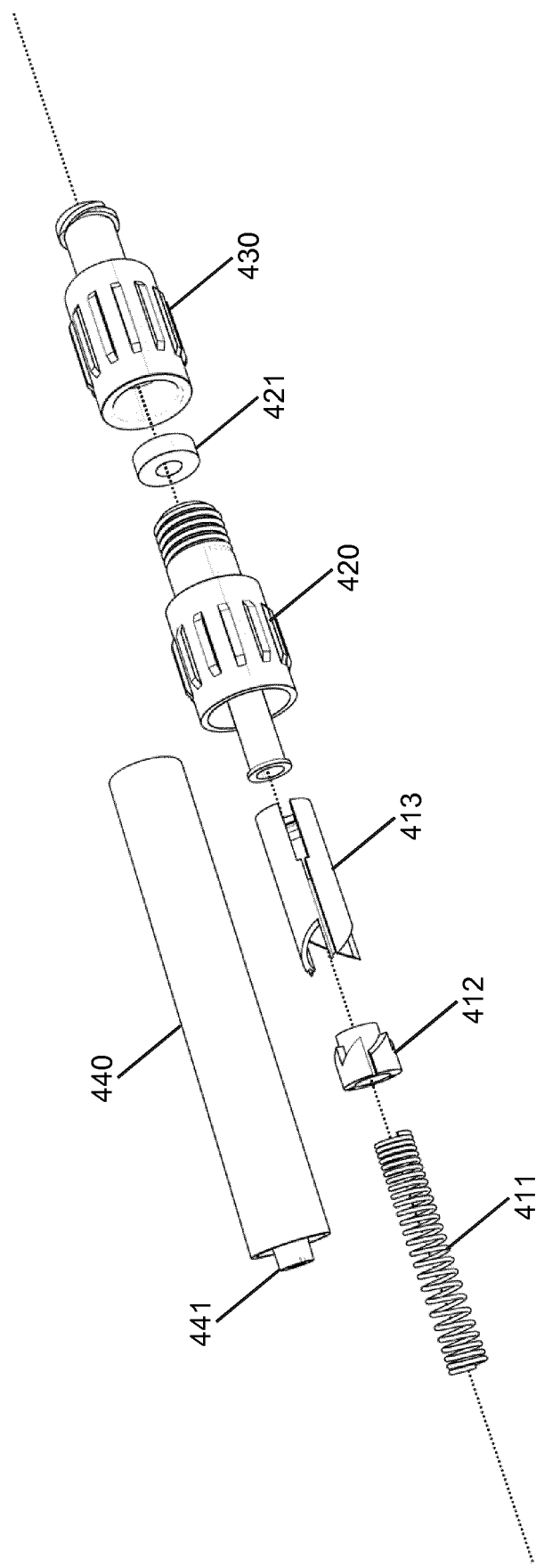
FIG. 4 is a perspective diagram illustrating the internal components of the FICS Lock-Grip Handle, as an embodiment.

The term "FICS Lock-Grip Handle" refers to an operational handle and positional stabilization device for maintaining the co-assembled functional units in relative order, alignment, and position (FIG. 4).

The term "FICS PTA Catheter" refers to a catheter formed to include a PTA inflation member at the distal end (FIG. 1) that can be combined with other functional units to form the "FICS LLS PTA Catheter" (FIG. 3).

Figure 1:
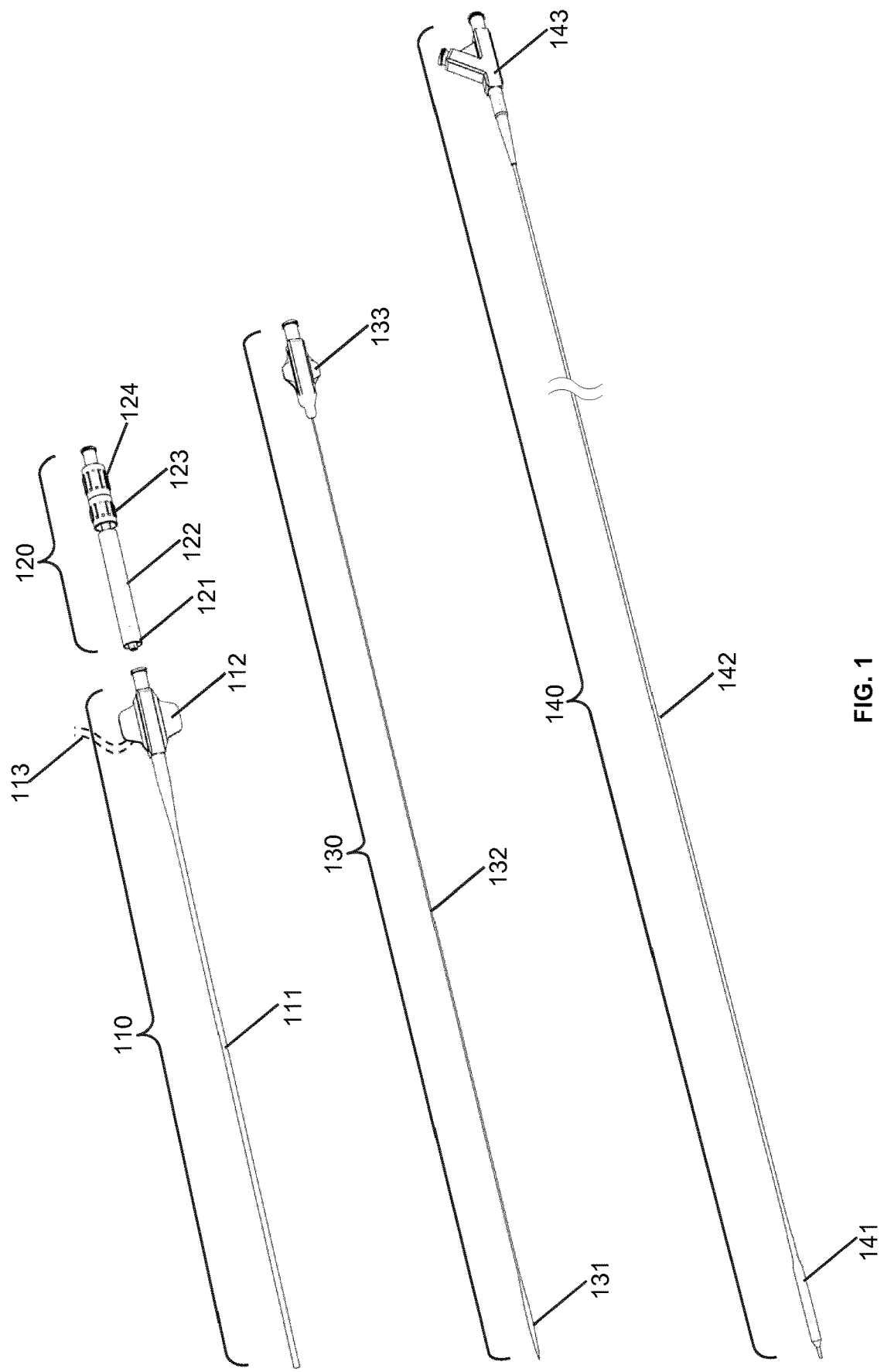
FIG. 1 illustrates the four main functional units of the Functionally Integratable Catheter System (FICS) of the present disclosure in a pre-configured state, as an embodiment.
Figure 10:
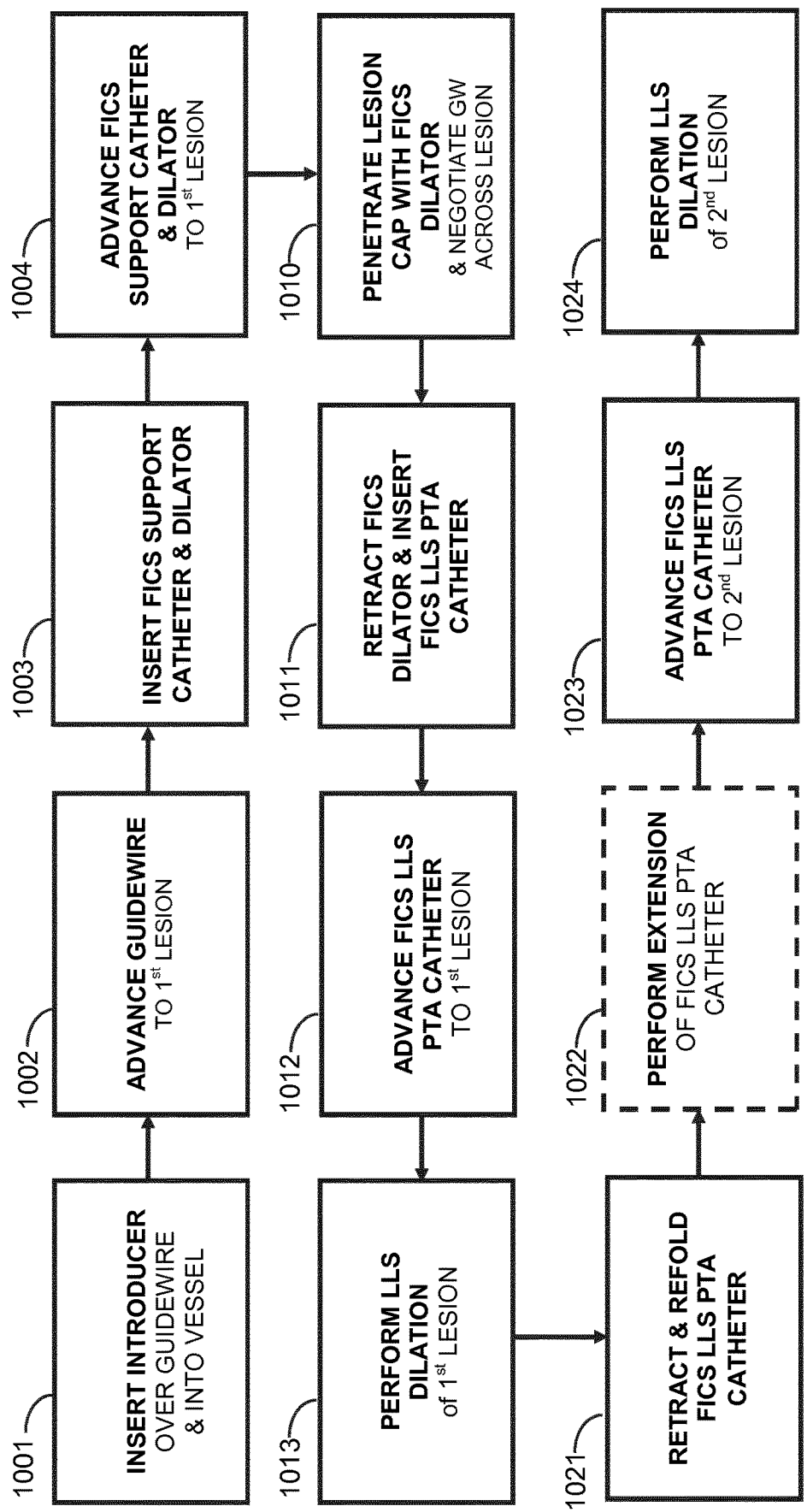
FIG. 10 is an exemplary flow diagram of a multi-staged angioplasty procedure performed in vivo for successive therapeutic treatment of complex lesions and CTOs utilizing the FICS System, as one embodiment.

The term "FICS LLS PTA Catheter" refers to the FICS configuration (FIGS. 3 and 13) resulting from functionally combining: (a) FICS Support Catheter (FIG. 1); (b) FICS PTA Catheter (FIG. 1); and (c) FICS Lock-Grip Handle (FIGS. 1 and 4). The balloon-length and balloon-diameter adjustability features of the FICS LLS PTA Catheter confer the "lesion-length selective" functionality (FIG. 14) for performing multi-level angioplasty procedures (FIG. 10).

The term "intraluminal recanalization" refers, for referencing the FICS System in this disclosure, to the restoration of perfusion through affected vessels by an interventional procedure mediated within the lumen of affected vessels, wherein the distal tip of the mechanically actuated Dilator is intended to function within the lumen of the treated vessels.

The terms "extraluminal recanalization" refers, for referencing the FICS System in this disclosure, to the restoration of perfusion through affected vessels by an interventional procedure mediated through the subintimal layers of affected vessels, wherein the distal tip of the mechanically actuated Dilator is intended to pass through the subintimal layers of the treated vessels before reentering the lumen at a site distal to a CTO or complex lesion. In effect, the "extraluminal recanalization" enables the creation of an alternative blood flow passage by forcibly separating the subintimal layers surrounding the CTO/complex lesion and forming an alternative conduit to restore perfusion.

The term "Total Length" (TL) refers to the total length of the FICS System or individual functional units.

The term "Usable Length" (UL) refers to the indwelling/working length portion of the FICS System or the individual functional units.

The term "Sheath Compatibility" refers to the maximum instrument outer diameter (OD) along the UL that can be introduced through an introducer sheath of commensurate inner diameter without resistance.

The term "guide wire compatibility" refers to the minimum inner diameter (ID) of the lumen of a functional unit/instrument for passing a guidewire of certain outer diameter without resistance.

B. Procedural Risks and Limitations of Current Medical Devices and Procedures for Treating Total Chronic Occlusions (CTO) and Complex Atherosclerotic Occlusions/Lesions Atherosclerosis can be generally classified into coronary, neurovascular or peripheral vascular disease subtypes, involving the progressive deterioration of cerebral, carotid, coronary, renal, hepatic, aortoilliac, iliac, gonadal, femoral, popliteal, and below-the-knee (BTK) arteries and veins. The diseased body can compensate for the gradual impairment of vascular functions by forming alternative collateral vessels in order to maintain adequate blood supply to dependent tissues and organs. However, such compensation mechanisms are only temporarily effective, and are marginally adequate for sustainably perfusing dependent tissues/organs. Insufficient perfusion of critical organs can have devastating effects, often resulting in one or more increasingly severe complications that can be triggered/exacerbated by atherosclerotic vessels, including: angina pectoris, myocardial infarction (MI) and congenital heart failure, often leading to patient mortality. Patients suffering from a peripheral vascular disease, resulting from the blockage of one or more peripheral blood vessels, are highly likely to experience the onset of multiple related complications (in the order of disease severity): claudication, ischemic rest pain, ulcerations, critical limb ischemia (CLI), gangrene, and/or tissue necrosis. In addition to raising the risks for requiring surgical interventional procedures, including bypass placement and limb amputations, some acutely life-threatening complications caused by vascular diseases may increase the risks for developing embolisms and strokes.

Lack of adequate perfusion through narrowed, stenotic, or occluded blood vessels can be treatable by various interventional procedures that can be suitably selected for patient-specific situations, taking into consideration several clinically relevant factors. In general, effective therapeutic interventions may involve systemic administration of one or more suitable pharmaceutical agent(s) in conjunction with minimally invasive, locally administered interventional procedures requiring the application of one or more atherectomy devices, balloon dilation catheters, and/or stents by a practicing clinician. For example, a balloon dilation catheter can be utilized for treating (a) coronary vessels during a "percutaneous transluminal coronary angioplasty" (PTCA); and (b) peripheral vessels can be utilized during a "percutaneous transluminal angioplasty" (PTA). However, if lesions, malformations, constrictions, obstructions and blockages within arteries/veins are not effectively treatable by standard vascular interventional therapy, then surgical intervention may be necessary, including "open surgery" effective for surgically forming a bypass composed of an autograft vein removed from a patient, or by forming a synthetic graft around the diseased vessel segment. However, if tissue damage is deemed irreversible beyond salvage, then bypass or surgical amputation of the affected limb may be the only option. Generally, surgical treatments can pose substantial risk and trauma for many symptomatic patients. Even if the outcome is deemed successful, the surgery may leave a profound and permanently debilitating impact on patients' mobility, life expectancy and overall quality of life.

As an effective and less risky alternative to drastic surgical procedures, interventional procedures have become more widely accepted and modestly practiced, if warranted by patient-specific circumstances. To propose treatment strategies and recommendations for the management of peripheral arterial disease, the European Society of Vascular Surgery and the World Federation of Vascular Surgery Societies have published the Trans-Atlantic Inter-Society Consensus document (TASC; 2000, TASC II; 2007). These recommendations provide general guidance for treating various types of lesions depending on their dimensions (length, diameter), degree of occlusion, and type of affected vessels. According to the "Consensus document," the "TASC A" lesions (least severe) have been deemed most suitable for endovascular procedures, and surgery has been primarily recommended for most severe cases, such as "TASC D" lesions. These "Type D" lesions can refer to either "chronic total occlusion" of the common or superficial femoral artery (>20 cm) involving the popliteal artery), and "chronic total occlusion" of the popliteal artery and proximal trifurcation vessels. However, endovascular therapy for complex lesions of the superficial femoral and popliteal artery remains controversial. This TASC document acknowledges that more clinical evidence may be required to base firm recommendations for treating TASC B and C lesions by PTA procedures. "Type B" lesions can be assigned for conditions involving multiple lesions (55 cm) (e.g., stenoses or occlusions); single stenosis or occlusion (515 cm) not involving the infrageniculate popliteal artery; single or multiple lesions in the absence of continuous tibial vessels to improve inflow for a distal bypass; heavily calcified occlusion (55 cm); and single popliteal stenosis. "Type C" lesions can be assigned for conditions involving multiple stenoses or occlusions (>15 cm) with or without heavy calcification, and recurrent stenoses or occlusions that have been previously treated by two endovascular interventions.

In particular, chronic occlusions represent a significant portion of vascular pathologies, and have historically presented a serious technical challenge for interventional practitioners that rely on conventional guide wires and catheters for accessing plaques/lesions. The treatment outcomes depend on the morphological and compositional characteristics of a given chronic total occlusion, in that softer and less compacted CTO plugs can be relatively easier to displace as compared to densely calcified CTO caps that may be impenetrable in the most challenging situations. Thus, "chronic total occlusions," which may be considered as a separate clinical pathology most commonly encountered in TASC D lesions, can remain procedurally challenging when treated by percutaneous transluminal angioplasty, contributing significantly to procedural failure rates for peripheral interventions. Despite the various technical challenges associated with CTO treatments, such minimally invasive interventional vascular approaches have been increasingly preferred as the first option for treating peripheral disease conditions to avoid substantial risk of mortality associated with conventional bypass surgery. Unfortunately, the success rates for intraluminal and subintimal CTO recanalization techniques as conventionally practiced using conventional guide wires and catheter devices remain only moderate at best. There is a persistent need to provide various patient-adaptable interventional devices that can be customized by physicians for more effective treatment of vascular conditions/diseases, such as associated complex lesions and CTOs.

As a first procedural step, percutaneous guidewire negotiation by intraluminal intervention can be attempted to cross and recanalize chronic occlusions. However, the application of standard guide wires and catheter devices to enable percutaneous intraluminal recanalization of CTOs have shown only moderate procedural success. Failure in guide wire negotiations can lead to failure in CTO recanalization. Factors that may significantly impact the prospective outcome include: lesion length, patient-specific anatomical tortuosity, lesion-cap calcification, medical operator skill and presence of run-off vessels. In more recent years, subintimal recanalization with distal reentry, known as percutaneous intentional extraluminal recanalization ("PIER"), has been increasingly advocated as a viable alternative approach when intraluminal passage remains procedurally unsuccessful. This technique has been applied with considerable technical success for superficial femoral artery (SFA) angioplasty, where multi-segmental, extended, calcified occlusions exhibiting mean occlusion lengths of 15 cm can be regularly observed.

Subintimal CTO recanalization approaches have been somewhat successful, although the technique itself may not be applicable in all cases. Typically, subintimal CTO recanalizations require most advanced levels of physician experience, skills, and general expertise because controlling the reentry into the true lumen of a target vessel and finding positional control of the reentry site can be potentially problematic for the inexperienced and/or unskilled. For example, vessel trauma and uncertain complications may result if reentry site is extended significantly and distally from the targeted vessel lumen region, thereby increasing the likelihood for subsequent subintimal angioplasty or stenting to be required inadvertently beyond the occluded vessel section. In the worst case scenario, improper guide wire negotiation for CTO recanalization can cause vessel trauma, rupture, dissection and/or bleeding due to inadvertent vessel wall perforation. A certain level of flexibility is desirable for guide wire tip sections and distal shaft portions, which enables efficient, atraumatic vessel navigation. When attempting CTO penetrations, however, this flexibility can cause the guide wire tip and shaft sections to buckle or kink, and can negatively impact the overall positional controllability of the guide wire, affecting device stability during implementation. The guide wire tip may be deflected from the typically hardened cap surface region of the CTO, causing the tip to veer eccentrically away from densely calcified plaque tissue into adjacent soft vessel walls. Once a subintimal passage has been inadvertently formed, the subsequent application of adjunct therapeutic devices, such as atherectomy catheters or balloon dilation catheters, can be substantially impeded or procedurally prohibited. Furthermore, the guide-wire penetration capability can be directly proportional to the shaft stiffness, which can be inversely proportional to having navigational flexibility, and therefore, the relatively flexible guide wire may require some additional form of guiding support to provide a safe yet effective measure of pushability.

As is the case for most medical devices, the various interventional devices and procedures for treating vessel occlusions have not satisfied all procedural challenges encountered during practical applications. Most interventional physicians must rely on device manufactures to provide all necessary equipment and implements in treating a broad spectrum of lesions/occlusions exhibiting different lengths, density, and severity. This limitation becomes acute especially for the treatment of complex lesions and total occlusions, where it is common for physicians to improvise in "arranging" their own "custom" devices by recombining various approved medical device components to devise a "make-shift" or workable combinations for those situations where a single pre-made device can be insufficient and alternatives are non-existent. Many medical devices and implements can serve multiple general functions and may not be designed for a specialized end use and/or devices made by different manufactures may not be functionally compatible to work together due to different material properties and/or dimensional configurations. Under the current circumstances, significant expertise and skill can be required to recanalize multiple numbers of chronic total occlusions in a single or multiple vessels. Significant physician judgement can guide procedural decisions as to the optimal combination of different medical device components to affect a desired therapeutic outcome. Technical challenges can include the selection and dimensional matching of various medical device components that can work well together during multi-staged, complex procedures. Seasoned expertise can be required for orchestrating the procedural combination of such medical device components that can be optimally positioned for highly variable, patient-specific clinical situations. An improved system would enable physicians of any skill level to effectively treat the most challenging and complex occlusions more conveniently in less time at significantly reduced cost.

C. Functionally Integratable Catheter System" ("FICS") for Treating Complex Atherosclerotic Lesions/Occlusions The present disclosure provides a comprehensive multi-functional device platform that can be variably configured by clinician operators for patient-specific anatomies and clinical situations for treating complex and total occlusions. This device platform enables physicians of any skill level to effectively treat the most challenging and complex lesions/occlusions more conveniently in less time. The present disclosure provides a Functionally Integratable Catheter System ("FICS System") representing a system of "functional units" that can be configured together to operate synergistically. FICS System comprises at least four main "functional units," including: (a) FICS Support Catheter; (b) FICS Dilator; (c) FICS PTA Catheter; and (d) FICS Lock-Grip Handle. Each "functional unit" can be provided in a pre-assembled form by the manufacturer, and optionally co-packaged as a device tray that includes the functional units (a) (d), intended to be configured into variable combinations ("FICS configurations") by clinician operators. In particular, examples of therapeutic-specific "functional sub-units" include the various "CTO Penetration Tips" and "Reentry Tips" disclosed herein, wherein each tip design can be designed specifically for treating a particular type of complex lesion and/or CTO. Any FICS configuration that includes the FICS Dilator incorporating a "CTO Penetration Tip" can be utilized for facilitating intraluminal recanalization. Any FICS configuration that includes the FICS Dilator incorporating a "Reentry Tip" can be utilized for facilitating extraluminal recanalization. Although each of the individual "functional units" may be operational in a pre-configured state, each functional unit may have limited functionality as a standalone device, as compared to the synergistic effect that can be achieved by utilizing the FICS System representing a comprehensive multi-functional device platform that can be highly adapted for treating any complex lesions and CTOs affecting both vascular and non-vascular tissues by providing several therapeutic-specific configurations as referenced in FIG. 15.

Many patients suffering from advanced atherosclerosis demonstrate multiple complex lesions along a common affected vessel, meaning that therapeutic intervention requires the sequential treatment (access, recanalization, and dilation) of all plaques/lesions in order to restore patency to sufficient levels. FICS provides a set of inter-operable functional units (a)-(e) conceptually analogous to a broad range of situation-specific implements that can be co-assembled by physicians. After employing a first hypothetical FICS configuration in a first interventional procedure (i.e., treatment of the first occlusion), the FICS functional units can be reversibly disassembled in order for the functional units to be reassembled into a different configuration for a second subsequent interventional procedure (i.e., treatment of the second occlusion), in the same patient if necessary. The cycle of dis-assembly and re-assembly may be repeated multiple times as necessary by clinical operators performing simultaneous and/or sequential applications in vivo. The interoperability of FICS functional units with a pre-deployed guidewire means that: (a) the FICS SC and GW can remain in situ without having to retract either of these for repositioning in order to treat a second or subsequent lesion present in the affected vessel undergoing treatment; (b) access to multiple number of lesions can be continuously maintained; (c) procedural steps can be reduced saving time/money; (d) quality of the procedure can be increased; and (e) operational convenience can be significantly improved.

Various embodiments are directed to the FICS components that can be assembled into various "functional units." Various embodiments are directed to the specific configurations that can be assembled together by combining different FICS "functional units" in order to be particularly customized for different types of vascular conditions in need of treatment. Various embodiments are directed to methods for manufacturing the FICS "functional units." Various embodiments are directed to the methods for treating vascular and/or non-vascular diseases utilizing one or more FICS configurations as a therapeutic implement for facilitating several functionalities, including more effective: (a) guide-wire negotiations; (b) lesion penetrations; (c) recanalizations; (d) vessel dilations; and (e) vessel-lumen restorations.

D. Co-Assembling the Functional Units of the Functionally Integratable Catheter System ("FICS")

The Functionally Integratable Catheter System ("FICS System") includes at least four main "functional units": (a) FICS Support Catheter; (b) FICS Dilator; (c) FICS PTA Catheter; and (d) FICS Lock-Grip Handle. These "functional units" can be designed to operate synergistically, and can be configured together by clinician operators before/ during multi-staged procedures for treating complex lesions/ total occlusions. In one preferred embodiment, all functional units can be packaged together as a device tray that includes functional units (a)-(d), intended for co-assembly into variable configurations by clinical operators (physician and/or operating professionals). In another preferred embodiment, each type of functional unit (a)-(d) can be packaged separately to be provided as a replacement component. All functional units can be configured and dimensioned for complete interoperability/compatibility.

In the following subsections, each of the referenced functional units (a)-(d) are described in further detail to specify respective structural and functional characteristics in FIGS. 1-15. Dimensional characteristics are described in the Examples and Tables 1-7. For convenience, FIG. 15 provides a flow-chart overview of the possible FICS System "configurations" as contemplated herein, providing a visual map of the various "functional units" and "functional sub-units" that can be selectively combined by a clinical operator for constructing therapeutic-specific "configurations" most effective for treating a broad range of complex lesions and CTOs.

1. Operational Configurations for FICS System 1.1 the Pre-Configured Functional Units of FICS System FIG. 1 shows the four main functional units of the Functionally Integratable Catheter System (FICS) of the present disclosure in a pre-configured state. In FIG. 1, the Functionally Integratable Catheter System (FICS) is represented as four separable components (from top to bottom): (a) Support Catheter 110; (b) Lock-Grip Handle 120; (c) Dilator 130; and (d) PTA Catheter 140, wherein these separable "functional units" can be co-assembled and re-assembled together by clinical operators in various combinations suitable for particular therapeutic purposes ("therapeutic-specific configurations"). The Support Catheter, the Dilator, and the PTA Catheter are each dimensionally adaptable for interoperability. The variable total length (TL) of the configured system is dimensionally adaptable within a range of approximately 90-220 cm, and wherein the variable usable length UL is dimensionally adaptable within a range of approximately 60-180 cm, further described in the Examples and Tables 1-7.

In FIG. 1, the FICS Support Catheter 110 comprises a shaft member 111, one or more flushing ports 113, and a manifold member 112 with a female luer lock adapter, which can be connected to the FICS Lock-Grip Handle 120 comprising a male luer adapter 121, an external casing member 122, a hemostatic valve portion formed within 123/124, and a female luer adapter. The support catheter further comprises a central lumen that receives the insertion of the dilator or the PTA catheter for enhancing maneuverability, and wherein the distal edge of the pre-configured Support Catheter is straight-edged for an interoperable design, unlike conventional Support Catheters having a tapered distal edge. The straight edge of the Support Catheter is a design feature that improves the interoperability between the Support Catheter and the Dilator/PTA Catheter when operationally joined; and is functionally augmented by insertion of other functional units to form a seamless, atraumatic edge upon their combination (e.g., FIG. 12A). The straight distal edge may include a reinforced tip region, wherein the reinforcement comprises a radiopaque material. As related embodiment, the FICS Support Catheter shaft and tip region can be formed from a flexible polymer, wherein the polymer may contain braided mesh embedded as structural reinforcement. The reinforced tubing and reinforced tip region can be designed to withstand positive and negative pressures exerted on the system, including both nominal balloon inflation pressure ranges and ranges exceeding burst pressure. At substantially the same time, the reinforcement can physically constrain the radial expansion of an inflatable member portion sheathed/coaxially received therein. Furthermore, such semi-rigid material compositions/combinations can provide for improved (a) device pushability; (b) directional bending capability; and (c) mechanical support for enhancing vessel guidance. As another embodiment, the FICS Support Catheter includes one or more flushing orifices that can be incorporated on the proximal lateral surface of the distal edge for providing and aspirating contrast fluid and saline solutions utilized during interventional procedures, wherein these orifices can be fluidly connected to the central lumen of the Support Catheter; and wherein the fluids can be transferred via one or more flushing ports (113) integrated into the SC manifold in the presence or absence of other insertable functional units. The flushing port can be integrated into the manifold as a separate luer inlet, or alternatively, the manifold may be configured to contain a two-way valve attached to the flushing port to enable media transport and to enable aspiration, perfusion and suction functionalities. The manifold may further comprise an additional balloon introducer and/or a hemostatic seal with an optional locking mechanism operationally coupled to the manifold to temporarily fixate/stabilize together multiple FICS functional units. As another embodiment, the FICS Support Catheter can include one or more distally positioned radiopaque markers placed along the shaft surface (e.g., proximal to the distal tip) to enable angiographic device visibility, such as for tracking the tip position within treatable vessels. As another embodiment, the FICS Support Catheter includes one or more visual or haptic surface markings for aiding the co-assembly of the FICS functional units as a positional guidance for user convenience (e.g., indicating the location of flushing holes). As another embodiment, the support catheter can be used as an introducer sheath within specific clinical use scenarios, for example, when performing an interventional procedure via radial or brachial access, thereby effectively reducing the number of components required. As related embodiment, the FICS Support Catheter can function as an aspiration catheter in the absence or presence of other FICS functional units.

In FIG. 1, the FICS Lock-Grip Handle 120 can function as a user handle for physician operators. As a critical operating element for FICS products, the Lock-Grip Handle 120 can provide relative positional stabilization (fixation, length adjustment and hemostatic sealing) for the interconnecting functional units, improving the general handling of the system and comprises a spring-loading mechanism for dilator tip propagation. The FICS Lock-Grip Handle can be designed as a simple polymeric cylinder, clip, wedge or screw that can be reversibly attached to the FICS Support Catheter or any of the following: FICS Dilator, FICS PTA Catheter. As another embodiment, the FICS Lock-Grip Handle can be attached at the proximal, non-indwelling shaft portion of the FICS Support Catheter. Operational coupling of the FICS Lock-Grip Handle to the other FICS functional units can provide relative positional stabilization, including longitudinal distance adjustment between the units. The internal hemostatic seal of the FICS Lock-Grip can be designed to accommodate coaxially receivable functional units of varying diameter. The FICS Lock-Grip Handle can include visual, acoustic or haptic markings for improved length adjustability and handling by clinical operators. As another embodiment, the FICS Lock-Grip Handle can be configured to simultaneously attach to the FICS Support Catheter and FICS Dilator in order to expose the balloon length formed between the FICS Support Catheter as the outer sheath and the inflatable member of the FICS Dilator. As another embodiment, the FICS Lock-Grip Handle can be provided firmly attached to the FICS Support Catheter, by methods known to persons skilled in the arts such as thermal or adhesive bonding, welding, gluing, screwing, snapping, clipping, interference fit, insertion and/or coaxial alignment. As another embodiment, the FICS Lock-Grip Handle can be mechanically coupled to coaxially receive the FICS Dilator by mechanically adhering, snapping, sliding, screwing, clipping, wedging or keying into the dilator shaft. As another embodiment, the FICS Lock-Grip Handle can include a hub, an adaptor, a connector, a fitting, a jack or a socket configured to receive an interlocking or mating surface element of coaxially receivable components. As another embodiment, the FICS Lock-Grip Handle provides a mechanical end stop, limiting the longitudinal displacement of either the FICS Dilator shaft, the tip, and/or the FICS PTA proximal balloon cone. The FICS Lock-Grip Handle is further described in FIG. 4.

In FIG. 1, the FICS Dilator 130 comprises a dilator tip 131, a shaft member 132 and a manifold member 133. The FICS Dilator can incorporate optional structural features to provide multiple functionalities. As related embodiments, the FICS Dilator may include: (a) a distally positioned, non-anchoring (non-inflatable) dilator tip segment having a single lumen configuration, wherein the lumen is a GW lumen; or (b) a distally positioned, anchoring and centering (inflatable) dilator tip segment with dual lumen configuration, wherein a first lumen is a GW lumen, and a second lumen is an inflation lumen that can be fluidly connected to the inflatable member; and c) an inner tubular member coaxially embedded into the aforementioned distal dilator tip segment, wherein the inner tubular member can be configured as a mechanically actuatable component, reversibly extensible along a length portion of the distal dilator tip, and can be sheathed/concealed therein during transport. The inner tubular member can be formed as a hollow bore hypotube, further comprising a tip (lancet). As another embodiment, the FICS Dilator can contain a substantially rigid tip region or segment (capable of occlusion penetration), which can be embedded or partially encapsulated within a tapered, substantially soft polymeric material, to facilitate atraumatic vessel guidance and effective occlusion penetration capability. As another embodiment, the rigid tip can be manufactured from a tubular member, such as a hypotube. In another embodiment, the tip and selected shaft regions of the FICS Dilator comprise elements and/or structures of dissimilar mechanical properties to facilitate variable stiffness portions along defined length sections of the dilator shaft. As another embodiment, the tapered dilation tip can form a seamless and atraumatic transition to the support catheter shaft or mantle. The distal shaft section of the FICS Dilator can have affixed one or more inflatable members that can function to controllably center and safely anchor the dilator in the target vessel region. As another embodiment, one or more distally positioned, radiopaque markers can be placed on the dilator shaft surface to enable angiographic device visibility for precise positional verification. The hypotube tip shape and construction may be modified to be suitable for forming an inflexible/non-malleable "CTO Penetration Tip" or a flexible/malleable "Reentry Tip." FICS Dilator is further described in FIGS. 2, 9 and 15. FICS Dilator is further described in FIGS. 2 A-B, 5-9, 10 A-B, 15, and 17. The FICS Dilator shaft can be designed to comprise of a substantially incompressible shaft material, such as a metal or a rigid polymer, and can be provided reinforced.

In FIG. 1, the FICS PTA Catheter 140 comprises an inflatable member (a balloon) 141, a catheter shaft 142, and a manifold member 143. The FICS PTA Catheter can incorporate standard features found in other PTA catheter products. However, in contrast to other PTA catheters, the FICS PTA Catheter includes an inflatable member portion of constant length that can be concentrically concealed within an outer sheath formed by the FICS Support Catheter. During operation, the balloon member of the PTA can be advanced from the distal portion of the Support Catheter, controllably exposing an inflatable portion of the balloon member to a desired length capable of effectively dilating the length of a target lesion situated along an affected vessel in need of treatment. The length of the inflated portion of the balloon can be adjusted to the length of the target lesion so that by providing a prolonged balloon of a fixed length (having an adjustable operational length ranging approximately from 0 to 30 cm), lesions of various lengths can be dilated/treated by adjusting the length of a single balloon that can be controllably inflated at desired lengths to match the respective lengths of target lesions typically encountered during intervention. For example, a shorter inflated portion of the balloon would be suitable for dilating the full length of a shorter target lesion of comparable length. Similarly, a longer inflated portion of the balloon would be suitable for dilating the full length of a longer lesion of comparable length. Furthermore, multiple radiopaque markings can be provided both a) at the distal end of the support catheter shaft; and (b) at the distal end of the balloon, to provide visual guidance for determining the length for the balloon exposed from the support catheter and in the inflated state. The variable usable length of the PTA Catheter correlates with the variable usable length of the inflatable member (balloon) by enabling a clinical operator to control the length of the balloon that can be exposed from the Support Catheter during the in vivo "lesion length selective" balloon dilatation process. First, the FICS PTA Catheter can be inserted into the FICS Support Catheter and stabilized utilizing the Lock-Grip Handle to form an in situ "length selective" FICS LLS PTA configuration capable of treating lesions of variable lengths utilizing a single prolonged balloon member that can be inflated at variable lengths. The FICS PTA catheter and the inflatable member portion can be reversibly removed from the FICS Support Catheter during operation. The length of the Support Catheter can be dimensionally configured so that a minimum balloon length (the recessed portion shown as functional dimension "C" of FIG. 13, and Table 2) can be restricted from inflating by maintaining permanently receded (sheathed) within the distal end of the Support Catheter during the inflation and deflation processes, to retain the original balloon folding capability for enabling multistage PTA treatments and to preserve the optimal shape of the inflatable portion of the balloon. The FICS PTA catheter shaft can be composed of a substantially incompressible material, for example a hypotube formed from metal or rigid polymeric or a reinforced shaft.

1.2 FICS Operational Configurations/Assembly of Functional Units

These separable "functional units" of the Functionally Integratable Catheter System (FICS) can be sequentially assembled/reassembled into different functional configurations, by physician operators, intended to be selectively adjustable for each phase of a multi-staged angioplasty procedure. The FICS configurations can be variably customized by a practicing physician to be suitable for different challenging situations encountered in treating patients who are seriously affected with advanced stages of arteriosclerosis (i.e., multiple lesions, extended lesion lengths, tortuous anatomy, total occlusions). For clinical situations involving chronic total occlusions, target obstructions must be either intraluminally penetrated (by passing through the CTO cap directly) or extraluminally circumnavigated (by passing through the subintimal vessel wall), before crossing and dilating the affected lesion/occlusion regardless of the variability in lesion length, lesion texture, and vessel anatomy. The presence of multiple lesions requires sequential treatment for each lesion/occlusion having certain length/texture characteristics. An ideal therapeutic instrument would be amenable to in vivo adjustment by a user for therapeutic-specific applications. The multi-configurational operation of the FICS functional units can provide a number of advantages: (a) procedural/clinical effectiveness in treating multiple and most severe complex lesions/CTO's; (b) substantial operational freedom/flexibility due to interoperable functional units enabled for reversible assembly; (c) substantial operational convenience for physicians; (d) substantial time savings for the benefit of both patients and physicians; and (e) quality PTA with comparably less dissections. FICS functional units can save procedural clinical time by enabling convenient interchangeability between different functional units so that physicians can quickly adapt the FICS functional units for each procedural phase, which may vary in procedural complexity depending on the characteristics of a treatable plaque/lesion (in terms of the number and dimensional variability) without the necessity for withdrawing the Support Catheter for each plaque/lesion treated sequentially thereby preventing loss of lesion access. For example, after employing a first hypothetical FICS configuration in a first interventional procedure (i.e., treatment of a first occlusion), the FICS functional units can be reversibly disassembled in order for the functional units to be reassembled into a different configuration for a second subsequent interventional procedure (i.e., treatment of a second occlusion), if necessary, in the same patient. The cycle of dis-assembly and re-assembly may be repeated multiple times as necessary by clinical operators performing simultaneous and/or sequential applications in vivo. The interoperability of FICS functional units involving a pre-deployed FICS Support Catheter means that the SC can remain deployed for enabling: (a) the continuous lesion access throughout the treatment of an affected vessel; and (b) the rapid exchange of other FICS functional units that may be insertable through the SC lumen for treating a second or subsequent lesion present in the same affected vessel, thereby eliminating the need for retracting the SC for repositioning, saving time, and improving operational convenience.

FIG. 2 illustrates the assembled "FICS Dilator configuration" adaptable for intraluminal and/or extraluminal recanalization. The FICS Dilator can be combined with the FICS Support Catheter to form the FICS "CTO Dilator" configuration, adapted with a suitable "CTO Penetration Tip" 205 in FIG. 2 for intraluminal recanalization. FIG. 8A provides a more detailed description of the "CTO Penetration Tip" shown as 205 in FIG. 2. FIGS. 7 A-D provide a detailed description on alternate projectable dilator tip designs having additional functionalities. FIGS. 5 A-B/6 A-B illustrate the operational mechanism for the mechanically actuated tips.

In FIG. 2, the Functionally Integratable Catheter System (FICS) in the "CTO Dilator" configuration can be assembled together by: (a) attaching the FICS Lock-Grip Handle 230 to the FICS Support Catheter 220; and (b) coaxially inserting the FICS Dilator 210 through the pre-assembled Support Catheter/Lock-Grip Handle described in step (a) so that the "CTO penetration" dilator tip 205 (also shown as 131 in FIG. 1 and explained in further detail in FIGS. 7 A-D, FIG. 8A) integrated into the distal end of the FICS Dilator can be positioned and locked length-wise to partially exit from the distal end of the FICS Support Catheter tubing, as shown. When co-assembled with the FICS CTO Dilator, the FICS Support Catheter can facilitate CTO penetration in a pressure and displacement controlled manner.

The FICS Dilator can be combined with the FICS Support Catheter to form the FICS "Reentry Dilator configuration," adapted with a suitable "Reentry Tip" 205 in FIG. 2 for extraluminal recanalization. FIG. 8B provides a more detailed description of the "Reentry Tip" shown as 205 in FIG. 2. FIGS. 7 A-D provide a detailed description on alternate projectable dilator tip designs having additional functionalities. FIGS. 12 A-B illustrate the operational mechanism for the mechanically actuated tips.

In FIG. 2, the Functionally Integratable Catheter System (FICS) in the "Reentry Dilator configuration" can be assembled together by: (a) attaching the FICS Lock-Grip Handle 230 to the FICS Support Catheter 220; and (b) coaxially inserting the FICS Dilator 210 through the pre-assembled Support Catheter/Lock-Grip Handle described in step (a) so that the "Reentry tip" 205 (also shown as 131 in FIG. 1 and explained in further detail in FIGS. 7 A-D, FIG. 8B) integrated into the distal end of the FICS Dilator can be positioned and locked length-wise to partially exit from the distal end of the FICS Support Catheter tubing, as shown. The dilator tip 205 is attachable to the dilator hub 210 via a tubular, elongated member (FIG. 1, item 132) e.g. formed from a hypotube. Particular examples of FICS Dilators utilizing a hypotube with "Reentry Tip configuration" for extraluminal CTO recanalization are shown in FIGS. 7 C-D and 8B. The dilator hub can be designed to be manually rotatable, enabling directional orientation of the conjoined tip portion. When co-assembled with FICS Lock-Grip and FICS Support Catheter, the FICS Dilator can facilitate CTO circumnavigation/subintimal access/reentry in a controlled manner with respect to directional orientation, pressure, and displacement. The Reentry Tip may be provided for simultaneous use with a designated CTO guide wire, in which the guide wire assumes a CTO penetration function, and the Reentry Tip in conjunction with the FICS Dilator Hub can provide a steering function for the guidewire. As an alternate embodiment, the Reentry Tip in conjunction with the FICS Dilator Hub can provide a steering function for the guide-wire in facilitating convenient side branch vessel access.

FIG. 3 illustrates the assembled "FICS LLS PTA Catheter configuration" useful for "lesion-length selectivity", as an embodiment. In FIG. 3, the Functionally Integratable Catheter System in the LLS PTA catheter configuration can be assembled together by: (a) attaching the Lock-Grip Handle 330 to the FICS Support Catheter 320; and (b) coaxially inserting the FICS PTA Catheter 310 through the pre-assembled Support Catheter/Lock-Grip Handle described in step (a) so that the inflatable member 305 (also feature 141 in FIG. 1 and explained in further operational detail in FIGS. 12-13), distally integrated into the PTA Catheter 310, can be positioned and locked length-wise to distally expose the inflatable member 141 to an adjustable length as desired. In this configuration, the length of the exposed inflatable member 305 represents the "lesion-length selective" portion of the FICS LLS PTA Catheter configuration as described herein. When co-assembled with the FICS Support Catheter, the balloon length can be specifically adjusted in viva to be adequately proportional to the target lesion length, enabling effective lesion treatment. By adjusting balloon length and appropriate inflation pressure, physicians can deploy a very flexible, high quality PTA balloon specifically suitable for the length and texture of a hypothetical lesion. Thus, the adjustable FICS configurations can increase the quality of the treatment, resulting in reduced frequency of dissections, increased procedural efficacy, reduced procedural time and cost. In this configuration, the FICS Lock-Grip Handle 320 can stabilize the position of the outer sheath formed by the FICS Support Catheter 310 relative to the position of the FICS LLS PTA Catheter by preventing proximal movement (recession) of the FICS Support Catheter 310 during balloon dilatation. FIGS. 10, 12 and 14 provide additional operational details of the "FICS LLS PTA" configuration.

FIG. 9 illustrates a perspective view of the FICS Dilator assembled with the FICS PTA Catheter, forming a steerable "LLS & Hypotube" dilator tip, useful for "lesion-length selective" anchoring/centering, as an embodiment. In FIG. 9, the Dilator configuration can be constructed by co-assembling all functional units shown in FIG. 1. In sequential order, the FICS Support Catheter 920 can be deployed over a pre-disposed guidewire, connecting a hemostatic valve 930 to the proximal end of the FICS Support Catheter, connecting FICS PTA Catheter 910 that can incorporate an inflatable member at the tip for anchoring into a target vessel adjacent to the CTO cap, connecting the Lock-Grip Handle 940 and connecting the FICS Dilator 950 that can incorporate a distal "CTO penetration" and/or "Reentry" tip. The balloon portion can be contained within an outer sheath formed by the FICS Support Catheter, similar to the inflatable dilator configuration in FIG. 7D. In this configuration, the FICS Lock-Grip Handle 1040 can stabilize the position of the outer sheath formed by the FICS Support Catheter 1020 relative to the position of the FICS LLS PTA Catheter by preventing proximal movement (recession) of the FICS Support Catheter 920 during balloon dilatation. Length adjustment can be facilitated by a Lock-Grip handle that serves as a displacement and locking element. In this embodiment, the "lesion-length selectivity" property of the FICS LLS PTA Dilation Catheter enables length-customizable vessel centering and anchoring in comparison to fixed length inflatable dilator configurations, having the additional benefit that the FICS LLS PTA Catheter configuration is already preassembled in place to straightforwardly enable consecutive treatments.

1.3 an Overview of Multiple FICS Configurations that can be Selectively Configured by Clinicians FIG. 15 is a flow-chart overview of the possible FICS System "configurations" as contemplated herein, providing a visual map of the various "functional units" and "functional subunits" that can be selectively combined by a clinical operator for constructing therapeutic-specific "configurations" most effective for treating a broad range of complex lesions and CTOs. Solid framed boxes and solid arrows of FIG. 15 indicate combinations of "functional units" and "functional subunits" that can be effective for a given therapeutic application. The dashed boxes and dashed arrows included in FIG. 15 indicate alternative combinations of "functional units" and "functional subunits" that may be configurable, if suitable for a given clinical situation.

In FIG. 15, the flow chart indicates certain therapeutic-specific "configurations" that can be selectively assembled by clinical operators as suitable for patient-specific situations. Starting at the top left of the diagram, 1500 represents the FICS System, resulting from the selective configurations (1510) of various "functional units" (1520) and "functional subunits" (1530) that can be assembled together by clinical operators. The three main FICS configurations in alignment with 1510 are shown as solid boxes: 1511 representing the "FICS LLS PTA configuration" (FIG. 3); 1512 representing the "FICS CTO Dilator configuration" (FIG. 2); and 1513 representing the "FICS Reentry Dilator configuration," (FIGS. 2 and 9) respectively from top down.

The "FICS LLS PTA configuration" 1511 can be configured by combining the following three main functional units represented as "solid" boxes: Support Catheter 1521, PTA Catheter 1523 and Lock-Grip Handle 1524 (individual functional units as illustrated in FIG. 1; configured in FIG. 3). The Dilator 1522 is represented by a dashed box to indicate that the functional units may be temporarily employed during the maneuvering of the Support Catheter 1521 and/or may be optionally included for user convenience. For example, the Dilator 1522 can be inserted into the Support Catheter 1521 (stabilized by the Lock-Grip Handle 1524) for effecting atraumatic maneuvering of the Support Catheter over the GW prior to administering the "FICS LLS PTA" configuration."

The "FICS CTO Dilator configuration" 1512 can be configured by combining the following three main functional units represented as "solid" boxes: Support Catheter 1521, PTA Catheter 1523 and Lock-Grip Handle 1524 (individual functional units as illustrated in FIG. 1; configured in FIG. 2). The PTA Catheter 1523 is represented by a "dashed" box to indicate that the functional unit is optional (e.g., suitable during the deployment of the Dilator configuration). The PTA Catheter 1523 (shown as a dashed box) is not part of the Dilator configuration because the PTA deployment becomes applicable only after achieving CTO penetration. In addition to selecting these main functional units, the clinical operators may select from several FICS Dilator designs options, each incorporating a unique distal tip design suitable for a given therapeutic application, by selecting from these options for constructing "CTO Penetration Tips": (a) non-inflatable, basic dilator tip 1534 (FIG. 7A) without anchoring and centering functionality (without an inflatable member); (b) non-inflatable, reinforced dilator tip 1535 (FIG. 7B) without anchoring and centering functionality, (c) a non-anchoring/non-centering basic dilator tip with a coaxially embedded hypotube 1536 (FIG. 7C) and (d) inflatable dilator tip with a coaxially embedded hypotube 1537 (FIG. 7D) with anchoring and centering functionality; wherein design options comprising a hypotube (FIG. 7C/D) can provide an additional directional/rotational steering capability about the length axis. Furthermore, the clinical operators may select from several dilator tip designs, each comprising a hypotube tip (formed as a lancet) having either a non-malleable, blunt-ended tubular member incorporated as a "CTO Penetration Tip" 1742 (FIG. 8A), or a malleable, tubular member 1745 embodied with a cutting edge (FIG. 8B) to configure a therapeutic-specific FICS configuration suitable for patient-specific situations. Furthermore, the FICS Dilator incorporating tip design 1542 (as illustrated in FIG. 8A) can be conjoined with other functional units such as the Support Catheter and the PTA Catheter for constructing therapeutic-specific configurations capable of intraluminal recanalization.

The "FICS Reentry Dilator configuration" 1513 can be configured by combining the following three main functional units represented as "solid" boxes: Support Catheter 1521, PTA Catheter 1523 and Lock-Grip Handle 1524 (individual functional units as illustrated by FIG. 1; configured in FIG. 2, 8B). The PTA Catheter 1523 represented by a dashed box is an optional functional unit. Clinical operators may select from several FICS Dilator designs options, each incorporating a unique distal tip design suitable for a given therapeutic application, by selecting from these options: (a) a non-anchoring/non-centering basic dilator tip with a coaxially embedded hypotube 1536 (FIG. 7C) and (b) inflatable dilator tip with a coaxially embedded hypotube 1537 (FIG. 7D) with anchoring and centering functionality; wherein design options comprising a hypotube (FIG. 7C/D) can provide an additional directional/rotational steering capability about the length axis. Furthermore, the clinical operators may select from several dilator tip designs, each comprising a hypotube tip (formed as a lancet) having either a non-malleable, blunt-ended tubular member 1742 (FIG. 8A), or a malleable, tubular member 1745 embodied with a cutting edge incorporated as a "Reentry Tip" (FIG. 8B) to configure a therapeutic-specific FICS configuration suitable for patient-specific situations. Furthermore, the FICS Dilator incorporating tip design 1745 (as illustrated in FIG. 8B) can be conjoined with other functional units such as the Support Catheter and the PTA Catheter (as illustrated in FIG. 1) for constructing therapeutic-specific configurations capable of extraluminal recanalization (as illustrated by FIGS. 2 and 9).

The "FICS Dilator," as part of the FICS System, can be provided as a therapeutically effective implement for performing intraluminal and/or extraluminal recanalizations for performing lesion length selective, multi-stage dilations, wherein the manufacture can provide several alternative designs for the Dilator by incorporating various subunits for constructing the therapeutic-specific dilator tip portions, such as: (a) a non-inflatable, distal polymeric member without anchoring and/or centering functionality; (b) an inflatable, distal polymeric member exhibiting anchoring and/or centering functionality; (c) a mechanically actuated, hypotube tip coaxially embedded into at least a portion of the distal polymeric member, capable of translational movement; (d) a mechanically actuated, hypotube tip coaxially embedded into at least a portion of the distal polymeric member, capable of translational and rotational movement; wherein the hypotube member can be provided conjoinable to the dilator hub; and wherein the hypotube distal tip portion can be formed either as a "CTO penetration Tip" or a "Reentry Tip" or as a tip conferred with the functionalities of both of these. As further embodiment, the inflatable, polymeric member can be formed by combining: (i) Support Catheter; and (ii) PTA Catheter. As a related embodiment, "CTO Dilator" and/or "Reentry Dilator" configurations may be formed by utilizing: a) Support Catheter; b) PTA catheter; c) Lock-Grip; and d) Hypotube formed with the "CTO Penetration Tip" and/or "Reentry Tip", wherein the Lock-Grip comprises a spring-loaded mechanism for the mechanical actuation of the hypotube member coaxially receivable therein.

2. Functional Unit Subassemblies 2.1. FICS Lock-Grip

FIG. 4 is a perspective drawing illustrating the internal components of the FICS Lock-Grip Handle, as an embodiment. In FIG. 4, the FICS Lock-Grip Handle comprises (from left to right): a spring element 411, a lower cam body 412, and an upper cam body 413, a proximal connector element 420, a hemostatic valve 421, and a shaft-locking handle 430, wherein these components can be connected as shown to enable operability. The spring element 411, the lower cam body 412, and the upper cam body 413 can be enclosed within an external casing member 440, which can be attached to a distal connector element 441 and the proximal connector element 420. The proximal connector element 420 can be coupled/connected to a shaft-locking handle 430 to achieve operational coupling, and the joined 420/430 unit can serve as "a pushing handle" for engaging the "mechanical actuation mechanism" (411, 412, and 413) contained within the external casing 440. The mechanical engagement between the "mechanical actuation mechanism" (411, 412, and 413) of the FICS Lock-Grip and the shaft member of the FICS Dilator or FICS LLS PTA Catheter can occur when the lower cam 412 can be mechanically engaged with the upper cam 413.

The FICS Lock-Grip Handle is an essential component of the FICS Dilator configuration (as shown in FIG. 2), and the FICS LLS PTA Catheter configuration (as shown in FIG. 3) by enabling the shaft member of either FICS Dilator or FICS LLS PTA Catheter to be coaxially engaged with respect to the FICS Support Catheter so that the distal tips of either functional units can be projected controllably in vivo through the distal end of the Support Catheter towards a target occlusion/plaque/lesion for achieving successful circumnavigation/penetration/crossing. The FICS Lock-Grip Handle can mechanically engage/disengage the shaft portion of either FICS Dilator or FICS LLS PTA Catheter so that relative translational movement and positioning of these components with respect to the FICS Support Catheter can be enabled. The FICS Lock-Grip Handle provides hemostatic sealing across the outer shaft portion to prevent excessive bleeding during device operation.

A shaft member of the FICS Dilator or FICS LLS PTA Catheter can attach reversibly to the Lock-Grip casing members 420 and 430 via the compressible seal 421 contained within the Lock-Grip Handle. To completely remove the FICS Dilator or FICS LLS PTA Catheter, the Lock-Grip Handle can be un-locked (disengaged), and the shaft can be pulled out of the Support Catheter, for example, after the completion of a CTO recanalization procedure. The independent integration of a spring-loaded tip-actuation mechanism and shaft-locking mechanism into the Lock-Grip Handle enables the operation of a single integrated device: (a) to independently facilitate hemostatic sealing in order to control/restrict blood flow through the treated vessel during the interventional procedure; (b) to mechanically engage/lock the shaft member to the FICS Support Catheter; (c) to mechanically project the dilator tip into the target occlusion/plaque/lesion; and (d) to transport fluid through the affected vessel to diagnostically visualize the interventional outcome and/or to effect adjunct therapies. The mechanical actuation mechanism can be dimensionally configured to co-axially accommodate either: (a) the FICS Dilator for enhancing the positional control over the dilator tip; or (b) the FICS PTA Catheter for enhancing the extension range of the PTA inflatable member. The FICS Lock-Grip can be maintained at the proximal hub section of the FICS Support Catheter throughout the intervention stages. For tip propagation, however, the controllable projection/translation of other FICS functional units, such as the LLS PTA catheter can be mechanically actuated, if desired, based on the same spring mechanism, wherein each incremental distance in tip propagation can be triggered by incremental spring compression, resulting in incremental exposure of the inflatable member portion.

2.2. Lock-Grip Actuation/Dilator-Tip Propagation Mechanisms

FIGS. 5 A-B illustrate cross-lateral views of "a dilator-tip propagation mechanism" (Style A) connected to the proximal end of the FICS Support Catheter, as one embodiment. In particular, FIG. 5A shows the dilator-tip propagation mechanism in the "tip-retracted" configuration, wherein the dilator tip of the FICS Dilator can be withdrawn within the distal end of the FICS Support Catheter. In contrast, FIG. 5B shows the dilator-tip propagation mechanism in the "tip-extended" configuration, wherein the dilator tip of the FICS Dilator can be extended from the distal end of the FICS Support Catheter. FIGS. 5 A-B represent two opposing configurations of the "dilator-tip propagation mechanism" that can be mechanically actuated by loading or releasing tension on a co-axially positioned spring member.

As an embodiment of Style A, the spring-actuated mechanism can be encased within a cylindrical outer casing 530, represented as rectangular cross-section in FIGS. 5A and 5B. The outer casing 530 can be shaped to form two main compartment sections having different functionalities: (a) a first internal compartment (at the distal end of the outer casing 530) can be shaped as a distal connector element 531 capable of operably engaging/connecting with a proximal hub portion 512 of the Support Catheter 510 as shown; and (b) a second internal compartment (at the proximal end of the outer casing 530) can be shaped to co-axially align the spring-actuated dilator-tip propagation mechanism components. The second internal compartment can include a "barrier" member 570 in contact with a portion of the inner luminal surface of the second internal compartment as shown, wherein the resulting compartment can have an uniform radial diameter to enable the co-axial movement of a co-axially positioned spring member 550, during spring expansion and compression cycles. The second internal compartment contains the spring member 550, which can be mechanically coupled to a lower cam 540, which can be mechanically coupled to an upper cam 560. When the upper cam 560 is mechanically engaged with the lower cam 540 by applying force towards the lower cam 540, both cams can move as a unit, as when a handle portion 544 of the distal hub 543 is pressed down once, causing the combined upper and lower cams to exert a combined distal longitudinal cam shaft movement. Furthermore, the lower cam 540 can be adhered to a hypotube member 520 so that when the lower and upper cams can be moved as a unit, proximally or distally with respect to the spring 550, the dilator tip positioned at the most distal end of the hypotube member 520 can move accordingly in the same direction as the movement of the cams 560 and 540. Both cams can be either: (a) moved away from the co-axial spring 550 that can increase the length of the spring as the spring relaxes (resulting in the "tip-retracted" position as shown in FIG. 5A); or (b) pushed against the co-axial string 550 that can reduce the length of the spring as the spring compresses (resulting in the "tip-extended" position as shown in FIG. 5B). The displacement of the spring member 550 that can cause the displacement of the dilator tip can be measured by the difference ΔL between the "tip-retracted" (FIG. 5A) and "tip-extended" (FIG. 5B) positions. The range of movement for the cams can be limited by placing a notch or protrusion member 531 proximal to the upper cam 540 that can make contact with the barrier member 570 to limit the spring compression. Alternatively, the protrusion member 531 can make contact with a proximal stopping member 531 to stabilize the upper cam 740 and attached components.

FIGS. 6 A-B illustrate cross-lateral views of "a dilator-tip propagation mechanism" (Style B) connected to the proximal end of the FICS Support Catheter, as one embodiment. In particular, FIG. 6A shows the dilator-tip propagation mechanism in the "tip-retracted" configuration, wherein the dilator tip of the FICS Dilator can be withdrawn within the distal end of the FICS Support Catheter. In contrast, FIG. 6B shows the dilator-tip propagation mechanism in the "tip-extended" configuration, wherein the dilator tip of the FICS Dilator can be extended from the distal end of the FICS Support Catheter. FIGS. 6 A-B represent two opposing configurations of the "dilator-tip propagation mechanism" that can be mechanically actuated by loading or releasing tension on a co-axially positioned spring member.

As an embodiment of Style B, the spring-actuated tip-propagation mechanism of FIGS. 6 A-B can be encased separately from a locking handle 680 that can be shaped to form a hemostatic valve portion capable of mechanically and operably engaging/connecting with the external surface portion of the hypotube 620. This is in contrast to the hypotube attachment mechanism utilized in "Style A" shown in FIGS. 5 A-B. "Style B" configuration combines a tip actuation mechanism and a shaft-locking mechanism to independently facilitate: (a) hemostatic sealing; (b) mechanical locking; and (c) tip extension at substantially the same or different time points. FIG. 4 provides a "Style B" configuration.

As an embodiment of Style B, the spring-actuated mechanism can be encased within an outer casing 630, shown as a rectangular cross-section in FIGS. 6 A and 6B. The outer casing 630 can be shaped to form two main compartments having different functionalities: (a) a first internal compartment (at the distal end of the outer casing 630) can be shaped as a distal connector 631 capable of operably engaging/connecting with a proximal hub portion 611 of the Support Catheter 610 as shown; and (b) a second internal compartment (at the proximal end of the outer casing 630) can be shaped to co-axially align the spring-actuated dilator-tip propagation mechanism components. The second internal compartment can be formed to include a set of guiding surface elements 670 (e.g. channels, grooves, tracks) along a portion of the inner luminal surface of the second internal compartment as shown, wherein the resulting compartment can have an uniform radial diameter to enable the co-axial movement of a co-axially positioned spring member 650. The second internal compartment contains the spring member 650, which can be mechanically coupled to a lower cam 640, which can be mechanically coupled to an upper cam 660. Both upper and lower cam bodies can be in mating contact with the guiding surface elements 670 to enable guided translational movement of the cam shaft components along a desired length portion within the casing 630. The upper cam body 660 can be translated beyond the position of the surface element portion 670, causing it to rotate to a different cam shaft height. The lower cam 640 can be adhered to a hypotube member 620, which is an integral component of the FICS Dilator. In Style B, the hypotube member 620 at the proximal end is extended through both cams and through the first handle 644, passing through a locking handle 680. The locking handle 680 includes a compressible seal 681 so that when connected to member 645 as shown in the tip-extended configuration (FIG. 6B), the compressible seal 681 expands radially so that any space between the components can be sealed almost completely to prevent blood flow from the catheters. In effect, the hypotube 620 can be reversibly attached to the upper cam shaft via the compressible seal 681 contained within the locking handle 680 so that the hypotube 620 can be operationally coupled to the tip-actuation mechanism. The FICS Dilator can be formed from a hypotube having a shaft member, 620, as shown. The hypotube shaft can be mechanically coupled to the lower cam body 640 by an elastomeric/compressible seal 681. The seal 681 can be compressed by rotating/screwing the handle 680 onto the lower cam body 640. Because the hypotube is relatively stiff/rigid, any translational movement of the hypotube shaft can be directly translated into dilator tip movement.

3 FICS Dilator and Tip Configurations 3.1. FICS Dilator

The FICS Dilator can be provided preconfigured with various features enhancing the convenient operability of the FICS Dilator in designated functional configurations. The respective tip configurations are described in detail hereafter. The FICS Dilator can be provided with anchoring/centering functionality (FIG. 7D) or without (FIGS. 7 A-C). Furthermore, the projectable tip portion can be provided with steering functionality (FIGS. 7 C-D) or without (FIGS. 7 A-B). Finally, the FICS Dilator can be provided as a "CTO Dilator" or as a "Reentry Dilator," depending on the tip configuration. As an embodiment, the FICS Support Catheter can be combined with the FICS Dilator to form the FICS "CTO Dilator configuration," having the "CTO Penetration Tips" shown in FIGS. 7 A-B or FIGS. 7 C-D and FIG. 8A, capable of performing intraluminal CTO recanalization. As another embodiment, the hypotube body that can be distally shaped as "CTO Penetration Tip" shown in FIG. 8A can be replaced by a hypotube body adapted with a "Reentry Tip" shown in FIG. 8B to yield a "FICS Reentry Dilator configuration" shown in FIGS. 7 0-D, that can be incorporated into the functional unit assembly shown in FIG. 2 and FIG. 9, capable of performing extraluminal CTO recanalization via subintimal access and reentry.

In general, the FICS Dilator can be designed to include at least: (a) a specifically configured, mechanically projectable tip constructed from a concentrically positioned hypotube to facilitate enhanced intra- and/or extraluminal recanalization of chronic total occlusion; and (b) a tapered, polymeric sleeve or shaft portions to provide a seamless transition from the guide wire to the distal end of the FICS Support Catheter for enabling enhanced, atraumatic passage, guidance and support. The FICS Dilator is configured for inter-operability with the FICS Support Catheter, which can provide substantial structural guidance and support as an external tubular shield. With respect to the exemplary FICS Dilator tip configurations described below in FIGS. 7-8, these FICS Dilator tips can remain receded within the GW lumen compartment of the FICS Dilator seated within the FICS Support Catheter to shield the vessel walls during transport and maneuvering operations, thereby avoiding potential vessel damage.

FIGS. 7 A-D illustrate cross-lateral views of four mechanically actuatable FICS Dilator Tip configurations, wherein FIG. 7A represents the "Basic Tip" style; FIG. 7B represents the "Reinforced Tip" style; FIG. 7C represents the "Basic & Hypotube" style; FIG. 7D represents the "LLS & Hypotube" style, as several embodiments. In FIG. 7A, a "Basic" "CTO penetration tip" 711 can be seamlessly fused against a single lumen, non-inflatable polymer member 720, wherein the tip portion formed by 711/720 fusion exhibits a constant circumference (along a defined tip length portion). The tip portion 711/720 of the FICS Dilator can exit from the distal end of the FICS Support Catheter 730. The CTO Penetration Tip can be formed as an elongated polymeric body 720, comprising a distal, tapered tip portion 711 and having a length section of uniform radial circumference adaptable to be receivable within an outer support catheter sleeve 730, as shown. In FIG. 7B, the "Reinforced" CTO penetration tip can be constructed differently from the basic tip style by incorporating a hardened tip section 712, which can be formed from substantially rigid materials, such as ceramics or metals for improving CTO penetration capability. The tip section can be attachable/insertable into the polymeric body 720, as shown. In FIG. 7C, the "Basic & Hypotube" style suitable as a "Reentry Tip configuration" differs from the "Basic Tip" configuration by incorporating an additional, coaxially alignable hypotube element 713, around which a polymeric body 720 can be formed. In FIG. 7D, the "LLS & Hypotube" style suitable as a "Reentry tip configuration" can be formed by simultaneously combining a coaxially insertable hypotube element 713 and the inflatable member 721 of the FICS LLS PTA catheter. Alternatively, the "Reentry" dilator tip 713 can be seamlessly fused to a radially expandable polymer member having two lumens 720, wherein the tip portion formed by 713/720 fusion exhibits an expandable diameter. The tip portion 713/720 of the FICS Dilator can exit from the distal end of the FICS Support Catheter 730.

This expandable configuration in FIG. 7D can be adjusted to fit vessels of variable diameters. The radially expandable polymer member 720 can serve as a "centering" balloon for improving vessel-anchoring capability for effective coaxially aligned (head-on) penetration of the "CTO penetration" dilator tip and consecutive guide wire passage through the CTO and/or for effective orientation-stabilized subintimal access/reentry of the "Reentry" dilator tip and consecutive extraluminal recanalization.

3.2. FICS "CTO Penetration" and "Reentry Tip"

FIGS. 8 A-B illustrate exemplary dilator tip designs for facilitating intraluminal and extraluminal recanalization. FIG. 8A is a magnified view of a "CTO Penetration Tip" comprising a non-malleable and blunt-ended hypotube of the FICS Dilator suitable for intraluminal recanalization, as an embodiment. In FIG. 8A, the "CTO Penetration Tip" of FIG. 7 C-D can be formed from a hollow-bore hypotube, having a substantially elongated tubular member 830 and a blunt-edged tip 811, as shown. The CTO Penetration Tip can be formed from a combination of one or more substantially rigid ceramic, polymeric or metal-based materials to enable the puncture and subsequent penetration of hardened, calcified CTO cap regions, wherein the tip can be independently formed as or be jointly affixed to a hypotube to further increase pushability while preventing or reducing any potential bending, buckling or kinking of the distal dilator shaft segment during CTO penetration. The FICS Dilator adapted with a "CTO Penetration Tip" is suitable in clinical situations in which direct CTO passage (utilizing the FICS Dilator adapted with a "CTO Penetration Tip") for effecting intraluminal recanalization may be desired.

FIG. 8B is a magnified view of a "Reentry Tip" comprising a malleable and angled hypotube of the FICS Dilator, suitable for extraluminal recanalization, as an embodiment. In FIG. 8B, the "Reentry Tip" differs from the "CTO Penetration Tip" presented in FIG. 8A particularly by the incorporation of a substantially malleable hypotube segment 820 that can be precisely cut (as slotted-tube or in a spiral pattern) into the hypotube member 820 and positioned in close proximity to the distal tip portion 813. The FICS Dilator adapted with a "Reentry Tip" is suitable in clinical situations in which direct CTO passage (utilizing the FICS Dilator adapted with a "CTO Penetration Tip") may be unsuitable. A FICS Dilator adapted with a "Reentry Tip" can be utilized in preparation for percutaneous intentional extraluminal recanalization, referred to as a "reentry procedure," which involves the following steps: (a) creating a directional cut into the subintimal tissue layer in proximal vicinity of a target CTO; (b) crossing the formed opening with a guide wire; (c) creating a directional cut into the subintimal tissue layer in distal vicinity of the CTO; (d) crossing the formed opening with a guide wire so that the CTO can be extraluminally circumnavigated; (e) performing a reentry into the true lumen of the vessel; (f) dilating the artificially formed extraluminal passage; and (g) restoring perfusion through the affected vessel. The exposable hypotube tip (lancet) section can be provided with a straight, angled, or shapeable tip orientation. The hypotube flexible tip may be initially provided, which can be further manipulated ex vivo into a particular shape of interest by the physician, for example by utilizing a pre-shaping tool, and loaded (retracted) in a pre-tensioned state into the Dilator/LLS via coaxial arrangement. By exposing the pre-tensioned segment, for example, by mechanical tip propagation, the tip can assume the pre-shaped configuration in vivo to facilitate optimized subintimal tissue penetration. The tip/shape can be formed out of a plastically/elastically deformable metal alloy. Alternatively, by forming the tip out of a pseudoelastic or superelastic alloy, including Nitinol, beneficial shape memory effects can be utilized. The edge of the distal tip can be formed through precision cutting and polishing, can be variably angled, for example, obtusely or acutely angled relative to the length axis to achieve a variably blunted or sharpened tip for improved shaft pushability and capability for efficiently cutting into the subintimal tissue layer in a directionally guidable manner.

In general, the mechanically projectable hypotube tip sections can be provided with a straight, angled, or malleable tip. The edge of the distal tip can be formed through processes of precision cutting and polishing, or can be variably angled (e.g., obtusely or acutely angled relative to the length axis) to achieve a variably blunted or sharpened tip for improving shaft pushability, directional control, and cutting efficiency into CTO and/or subintimal tissue during penetration. As an embodiment, the flexible reentry tip can be blunt-edged to minimize the risk of vessel perforation during subintimal access. In another embodiment, the CTO penetration tip may be provided with a flexible segment to enable simultaneous CTO penetration and/or reentry capability. The inner tubular member forming the hypotube may comprise a combination of metals and polymers as indicated throughout the specification. The dilator tips can be actuated by a spring mechanism embedded into the FICS Lock-Grip handle and as illustrated/described in FIGS. 4-6. The FICS Dilator unit can be configured for simultaneous operation of the FICS Support Catheter, which can provide substantial structural guidance and support as an external tubular shield. For both configurations, the FICS Dilator can be placed within the lumen compartment of the FICS Support Catheter to shield either "CTO penetration" or "Reentry" tip during transport through the affected vessel, thereby minimizing potential vessel wall damage.

4. Operational Characteristics of FICS System 4.1 FICS LLS PTA Dilator Configurations Capable of Lesion-Length Selectivity for Multi-Staged Procedures FIG. 10 is an exemplary flow diagram of a multi-staged angioplasty procedure performed in vivo for successive therapeutic treatment of complex lesions and CTOs utilizing the FICS System, as one embodiment. In FIG. 10, as the first step 1001, an introducer sheath can be inserted to enable vascular access of catheter devices under hemostatic conditions. In step 1002, the predisposed guide wire can be controllably advanced to the target treatment area and positioned across the lesion. In step 1003, the FICS Support Catheter can be inserted simultaneously with the FICS Dilator through the lumen of the introducer sheath and over the predisposed guide wire. In step 1004, the FICS Support Catheter and FICS Dilator can be controllably and simultaneously advanced over the propositioned guide wire to the first intended treatment area, such as a first hypothetical complex lesion. In step 1010, the FICS Dilator tip (also "CTO Penetration Tip") can be controllably advanced into the hardened surface cap of a CTO to facilitate guide-wire negotiation and CTO penetration. In step 1011, the FICS Dilator can be retracted, and the FICS PTA Catheter can be inserted. In step 1012, the FICS PTA Catheter can be controllably advanced via the predisposed FICS Support Catheter and over the predisposed guide wire to a first, complex lesion. In step 1013, the distal working end of the formed FICS LLS PTA Catheter can be utilized to "length-selectively" treat the lesion and restore luminal patency at the first intended treatment site. This step enables the angiographic visibility of lesions distally located in the affected vessel. After deflating and retracting the length selective balloon element back into the FICS Support Catheter in step 1021, the flushing holes of the FICS Support Catheter can be used for injecting contrast agent to enable angiographic follow up. As an optional step 1022, if additional lesions may be observable along the same affected vessel, the usable length portion of the FICS LLS PTA Catheter can be manually extended by the physician while maintaining the current position of the guide wire within the intended treatment site. The predisposed guide wire can be controllably advanced to the next target treatment area and the distal end of the guide wire across the second lesion can be positioned. In step 1023, the physician can controllably advance the optionally extended FICS LLS PTA Catheter together with the FICS Support Catheter over the prepositioned guide wire to the next intended treatment area, such as a second lesion. In step 1024, the distal working end of the optionally extended FICS LLS PTA Catheter can be utilized to treat length-selectively the lesion and restore luminal patency at the second intended treatment site. The number of treatment sites utilized in this flow diagram is exemplary in nature and can include an arbitrary number of successive treatment sites, provided that the length of the predisposed guide wire, the length of the support catheter, and the adjustable usable length portion of the catheter in extended configuration enables access to successive target treatment areas.

4.2. CTO Penetration by Dilator Tip Propagation

FIGS. 11 A-D illustrate cross-lateral views representing four consecutive configurational stages A-D for mechanically propagating the "CTO penetration tip," as one embodiment.

Figure 11A:
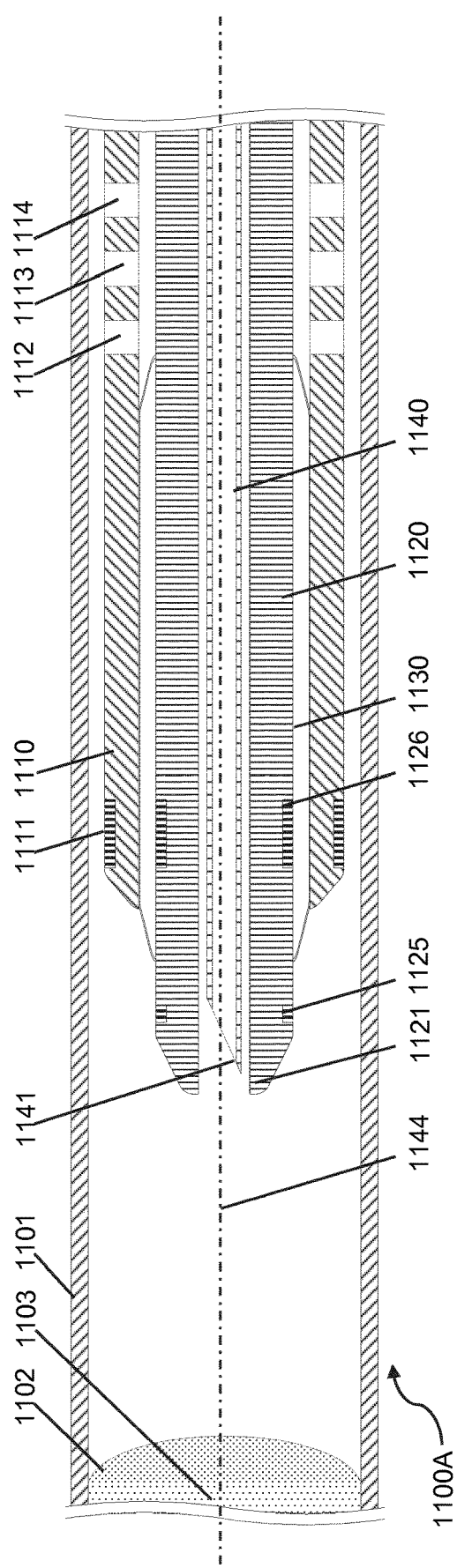
FIGS. 11 A-D illustrate cross-lateral views representing four consecutive configurational stages A-D for mechanically propagating the "CTO penetration tip," as one embodiment.

In FIG. 11A, a cross-lateral view of an occluded vessel 1100 amenable for treatment is shown at the first hypothetical stage, including a vessel wall 1101, a hardened CTO lesion cap 1102 and softer lesion tissue 1103. FICS Support Catheter 1110 is illustrated as an elongated tubular member concentrically situated in the affected vessel and positioned along the vessel length axis 1144, and can incorporate a radiopaque marker band 1111 located on a distal tip region, and one or more proximally positioned flushing/aspiration holes 1112, 1113, 1114. The FICS Dilator can be inserted concentrically within the lumen space of the predisposed and temporarily stationary FICS Support Catheter shaft 1110, and can be longitudinally positioned with respect to the length axis of the FICS Support Catheter, so that a proximal radiopaque marker 1126 located on the FICS Dilator shaft 1120, and an inflatable member 1130, can be positionally aligned with a substantially similarly sized radiopaque marker 1111 located near the distal end of the FICS Support Catheter. Alternatively, a differently sized radiopaque marker 1125 proximately near the tapered, distal dilator tip portion 1121, and one or more of the radiopaque markers 1111 can be aligned to indicate adequate tip positioning and proper atraumatic alignment between the FICS Support Catheter and FICS, if desired. At this stage, it is noted that inflatable member 1130 is substantially folded within the FICS Support Catheter. The anchoring capable dilator tip configuration utilized is substantially similar to the configuration shown in FIG. 7D.

Figure 11B:
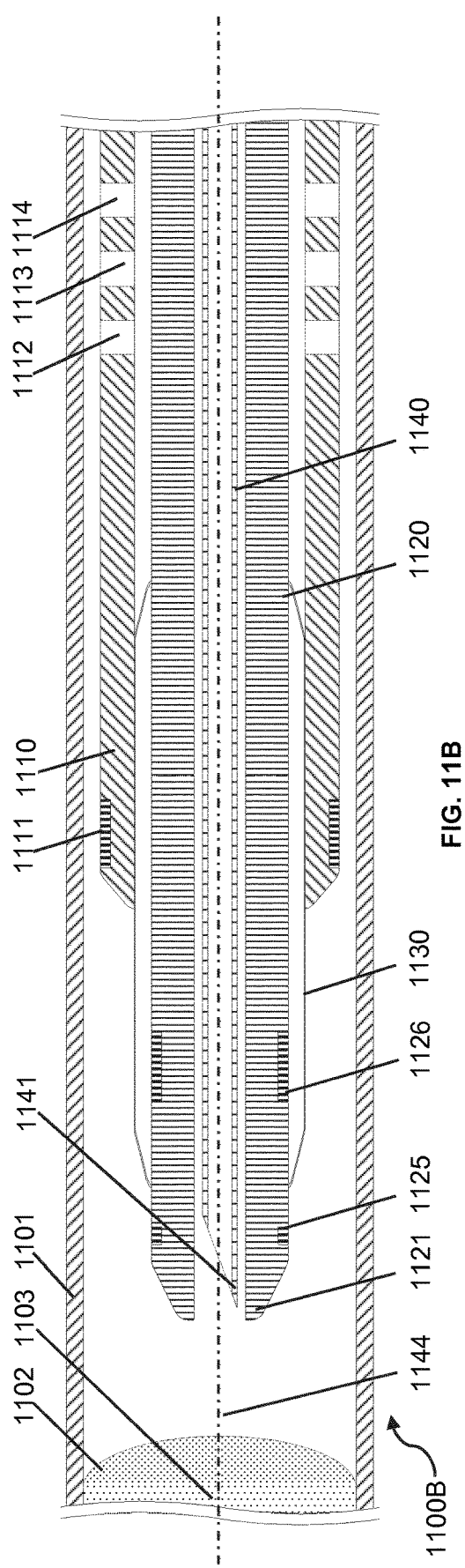

In FIG. 11B, the cross-lateral view of an occluded vessel 1100 amenable for treatment is shown at the second hypothetical stage, wherein the FICS Dilator shaft 1120 can be transposed distally in parallel with the length axis of the FICS Support Catheter 1144 and positioned in close proximal contact with the lesion cap 1102. The relative positions for FICS Dilator and FICS Support Catheter can be angiographically verifiable by the equidistant positioning of the three radiopaque markers 1111, 1125, and 1126. At this stage, the inflatable member 1130 of the FICS Dilator in an uninflated state can partially exit in distal direction from the FICS Support Catheter 1110. The extension range of the inflatable member portion can be lengthwise configured as such that a desirable proximal length portion thereof can remain seated within the Support Catheter even in fully extended condition. This particular configuration can provide improved proximal balloon cone formation and enables controllable refolding of the inflatable member upon retraction.

In FIG. 11C, the cross-lateral view of an occluded vessel 1100 amenable for treatment is shown at the third hypothetical stage, wherein the inflatable member 1130 of the FICS Dilator can be inflated for vessel centering and anchoring in preparation for CTO penetration. Once anchored radially into the vessel, the "CTO penetration" distal tip 1141 of the FICS CTO Dilator can be fully extended distally, conferred by the spring-actuation mechanisms described in FIGS. 4-6 in order to penetrate the hardened lesion cap 1102 in preparation for guide-wire negotiation.

In FIG. 11D, the cross-lateral view of an occluded vessel 1100 amenable for treatment is shown at the fourth hypothetical stage, wherein the penetrated lesion cap 1102 can be negotiated with a guide wire 1150 to facilitate guide wire crossing across the remaining lesion in preparation for lesion dilation.

4.3 Lesion Length Adaptability for Successive Multi-Stage Treatment

FIGS. 12 A-D illustrate the inter-operability of the functional units for enabling in vivo "lesion-length selectively" and deploying the FICS LLS PTA configuration in successive multi-level stages, as an embodiment.

In FIG. 12A, the LLS PTA Catheter 1212 can be coaxially inserted into the FICS Support Catheter shaft 1220 through the associated support catheter hub 1221 and via the attached FICS Grip-Lock Handle 1230. The distal tip portion 1210 of the FICS LLS PTA Catheter can exit from the distal end of FICS Support Catheter shaft 1220 to form a seamless transition with the catheter shaft. The relative position between the FICS LLS PTA Catheter and the FICS Support Catheter end can be dialed in using the mechanical locking feature of the Lock-Grip Handle 1231 and the surface markings 1211 present on the proximal FICS LLS PTA Catheter shaft. The Lock-Grip Handle 1231 can be mechanically engaged (screwed shut via the hemostatic valve seal 1231) to lock the current position of the FICS LLS PTA Catheter tip to ensure atraumatic passage of the FICS components along affected vessels. The configuration shown in FIG. 12A is optimal for advancing the FICS LLS PTA Catheter to the target treatment site.

In FIG. 12B, the FICS Lock-Grip Handle can be disengaged (the hemostatic valve screw/seal 1231 is moved to an open position as indicated by the dashed arrow) to facilitate the lengthwise distal propagation of the FICS LLS PTA Catheter through the FICS Lock-Grip Handle and FICS Support Catheter. In FIG. 12C, the FICS Lock-Grip Handle can be reversibly engaged to lock the selectively exposed length portion of the inflatable member 1250. The configurations shown in FIG. 12B/12C are optimal for in vivo length selective adjustment of the inflatable member portion of the FICS LLS PTA Catheter at the target treatment site. In FIG. 12O, the FICS LLS PTA Catheter can be inflated along the predialed exposed length portion, as shown. The configuration shown in FIG. 12D is optimal for lesion dilatation.

FIGS. 14 A-B illustrate cross-lateral views of the in vivo "lesion-length selective" feature of the inflatable member for the FICS LLS PTA Catheter for successive lesion treatments, as one embodiment.

In FIG. 14A, a hypothetical vessel 1400A is shown, having a first lesion 1402 and a second lesion 1401. On the right, the inflatable member 1420 of the FICS LLS PTA Catheter can be exposed from the distal end of the FICS Support Catheter 1430, wherein the length of the inflatable member 1420 can be selectively adjusted to the length of the lesion (L1), angiographically verifiable through the distance formed between radiopaque markers 1421 and 1431, the first marker incorporated into a distal inflatable member portion, the second incorporated into a distal support catheter shaft portion, and correlatingly positioned at either end of the lesion length of the first lesion. The inflated balloon can be controllably dilated along the lesion length by radially exerting pressure perpendicular to the surface of the lesion until the recanalized lesion can be widened substantially to restore luminal patency.

In FIG. 14B, the hypothetical vessel 1400B is shown, wherein the first lesion 1402 has been treated successfully, and the FICS LLS PTA Catheter has been repositioned, with the inflatable member portion shown controllably extended so that the length of the inflatable member 1420 can be aligned with the length of the second lesion 1401 (L2). When the balloon is dilated, the pressure can be radially exerted against the surface of the lesion until patency is restored in the second lesion. The procedure can be repeated as many times as necessary using the FICS configurations described herein.

5. Dimensional Characteristics of FICS System

To construct therapeutic-specific configurations of the FICS System of the present disclosure, the individual "functional units" and "functional subunits" of the FICS System must be designed so that the dimensional specifications of these components ("FICS specifications") are interoperable over a broad operational range. For example, catheters, PTA balloons, dilators, and guide wires are generally manufactured as set of variable products that provide several sizing options for selecting instrument length and instrument diameter that can cover a broad range of procedural applications. Because the FICS System is intended to provide a comprehensive medical device platform for treating a broad range of complex lesions and CTOs, the dimensional operational range for each critical component of the FICS System components can be determined. The specific interoperability and dimensional specifications for the FICS System components can be described in reference to a hypothetical "FICS LLS PTA catheter configuration" in FIG. 13, which is described in Examples 1-7 below.

6. Manufacture and Material Selection for FICS

In general, any components of the FICS platform can be constructed by utilizing the methods known to persons skilled in the art. Dilator and/or inflatable members of both Dilator and PTA catheter can be constructed substantially in cylindrical form, having uniformly positioned mantle surfaces along a longitudinal axis, wherein the length sections shaped with a variable tapering profile can be attached to form defined cone regions of the polymeric body/balloon. The dilation elements (polymeric body/balloon) can be located at the distal end of the indwelling FICS catheter during treatment. The inflation can be typically facilitated by incorporating one or more lumens, wherein at least one lumen can be in fluid communication with the elongate, inflatable member, and wherein one or more lumen(s) can facilitate inflation and transport contrast agents and other fluids. FICS PTA Catheter may comprise at least a guide wire lumen and an inflation lumen, provided as dual lumen configurations in side-by-side or coaxial (nested) arrangement. These lumen configurations can be provided as extruded tubing, forming the "inner member," as opposed to the outer member, or catheter shaft. Inner member comprising the one or more lumen and the outer member, or a catheter shaft can be designed to have a fixed length or length adjustability.

All FICS functional units intended for insertion into the SC can be designed to be guidable with a guide wire along the complete length of the instrument, so that the guide wire can enter at the distal tip and exit at the proximal hub. For PTA catheters, such a design can be referred to as an over-the-wire ("OTW") configuration. In contrast to the OTW type of balloon dilation catheters, the rapid exchange (RX) type of balloon dilation catheter instruments can be operated with a significantly shorter guide wire length. Such catheter types can contain a guide wire exit port proximally positioned at a defined distance from the distal tip, so that the guide wire can be contained only within a limited, distally positioned guide wire lumen length or section, and does not need to extend along the complete inner guide wire lumen length. Whereas normal RX ports may be configured as single, annular openings exiting from a proximal position of the GW lumen through the instrument shaft, FICS requires the RX port of insertable functional units to be constructed as a slitted slot maintained over a significant shaft length portion. With respect to the FICS system, the insertable FICS Dilator and PTA catheter components may benefit from an RX port for enabling decreased GW lengths, particularly for systems having a usable length exceeding 150 cm.

The FICS catheter components can be manufactured from biocompatible, polymeric, metallic and ceramic materials. For example, the catheter components may be manufactured from aliphatic, semiaromatic and aromatic polyamides; polyether ether ketones (PEEK); polyimides; linear and nonlinear, branched or nonbranched, low molecular weight, medium molecular weight, or high molecular weight; low density, medium density, or high density polyolefins, including polyethylene and polypropylene, silicones, thermoplastic elastomers, such as polyurethanes (TPEs) and fluoroelastomers, polycarbonates, polyethylene terephthalate (PET) and combinations, including blends and copolymers of any of these materials.

The FICS catheter components can also be fabricated as a single layer, dual-layer, or multi-layer configurations. In the instance of dual-layer or multi-layer configurations, certain catheter elements, including for example the shaft and the balloon, may utilize the same material for each layer or may utilize different materials for each layer. The multiple layers can be glued, melted or fused together with an adhesive or employing a co-extrusion process. Alternatively, the multiple layers are not required to be attached or glued together, instead, the multiple layers may be allowed to move independently. Additionally, the durometer of the material(s) selected for each layer may be altered to further alter the performance aspects of the individual catheter components. Also, the chemical functionality and/or physical polarity of the material can be changed to enhance interfacial adhesion between the differing layers and/or to provide exposed surfaces and/or inner lumen with an increased lubriciousness or changed surface energy when in contact with a guide wire, injected liquids, or functional coatings, for example.

These chemical and physical treatments or alternations/variations may include for instance chemical additives that can introduce another chemical functionality to the interfacial surface, when added to an exemplary base polymer formulation intended to form one or more layers of the catheter component, for example, including functional groups such as carboxy- and/or amino groups, which can effectively enhance the underlying polarity of the layer and the substrate, thus facilitating enhanced adhesion and mechanical fixation strength in between one or more layered structures of catheter components.

Other surface modifications or plasma techniques can be employed for changing the chemical and/or the mechanical properties of the underlying substrate, wherein the plasma modification of the material(s) may affect the polarity and/or the surface energy of the balloon layer(s). Other suitable techniques may incorporate additives, adhesives and/or filling agents, which can introduce other beneficial properties to catheter materials. For example, the catheter shaft or the balloon may incorporate radiopaque elements embedded within polymeric materials to selectively increase fluoroscopic visibility at desired shaft locations. Additionally the shaft may incorporate fluoropolymer-based filler particles/fibers to permanently decrease the frictional coefficient as compared to an untreated base-polymer formulation or activatable, single-use coatings. Furthermore, the shaft can be reinforced and may contain metal or polymer-based strands, fibers, wires, braids, meshes and/or fabrics embedded as layers, sections or regions into the base-shaft material.

The FICS catheter components can be manufactured by following various methods known to persons skilled in the art, including single-, dual-, and or multilayer extrusion, blow molding, dip molding, deposition or other manufacturing methods suitable for manufacturing FICS catheter components. The material for forming FICS catheters may be subjected to mechanical processes before, during or after the catheter manufacture. If an extrusion process is utilized for the manufacturing process, the tubular member for forming the shaft member can be stretched before or during the extrusion process. The temperature, the extrusion pressure, or other parameters can be changed during the manufacturing processes to affect the properties of the manufactured shaft.

EXAMPLES

Example 1

Functional Dimensions of FICS System

Figure 13:
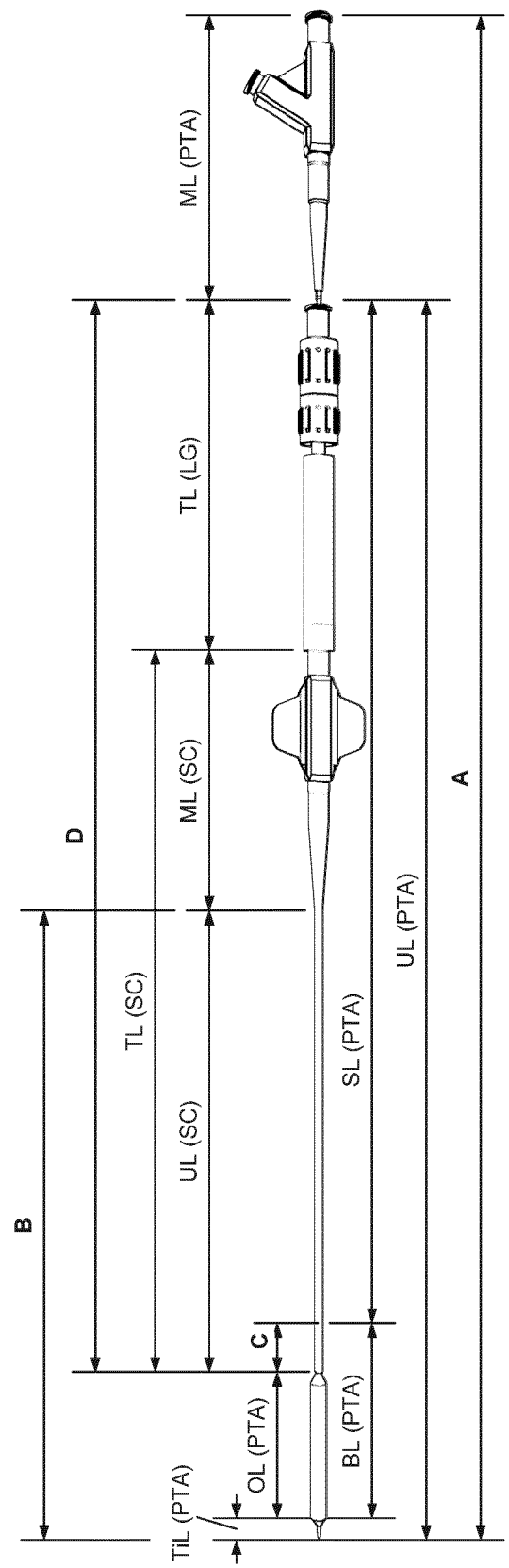
FIG. 13 is a dimensional diagram of a FICS System in a fully extended LLS PTA Catheter configuration, showing the relative dimensional interoperability of the individual "functional units" and "functional subunits" as a convenient reference.
Figure 14:
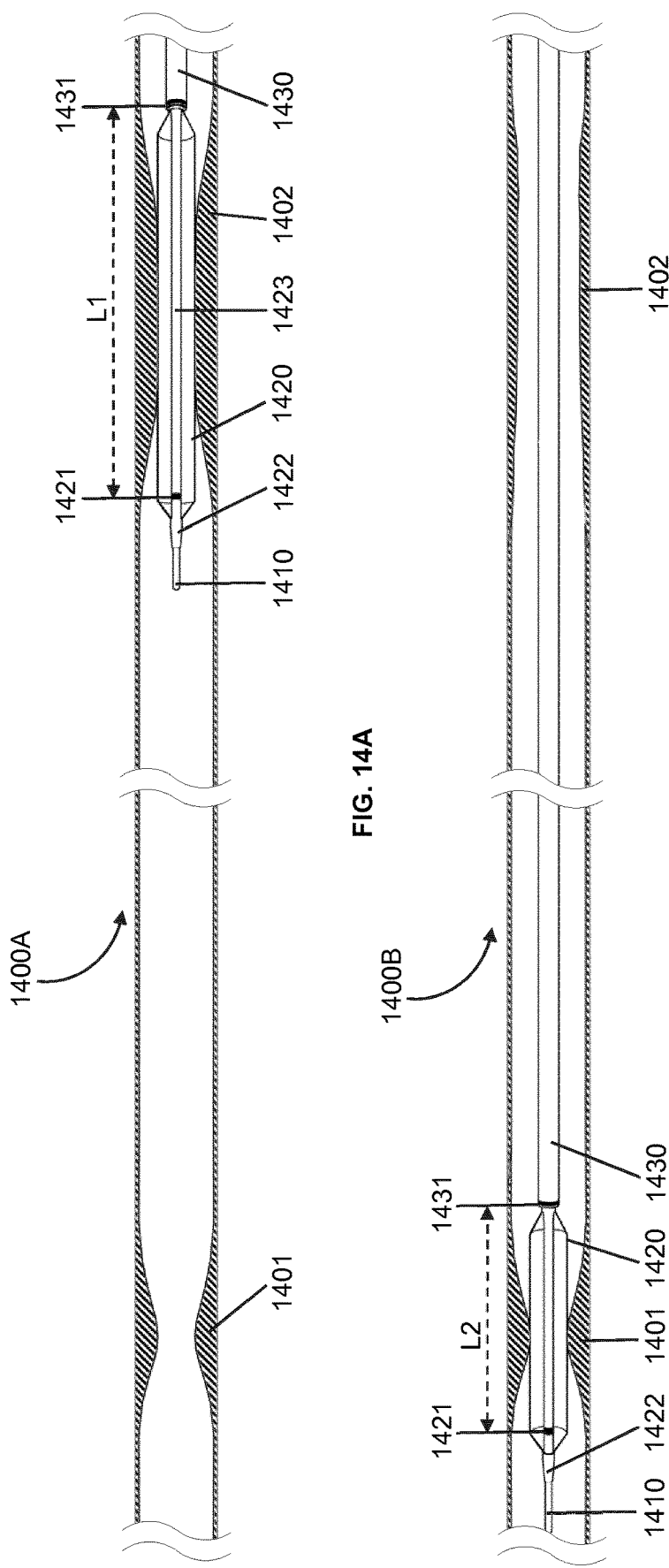
FIGS. 14 A-B illustrate cross-lateral views of the in vivo lesion-length selective feature of the inflatable member for the FICS LLS PTA Catheter for successive lesion treatments, as one embodiment.

FIG. 13 is a dimensional diagram of a FICS System in a fully extended "LLS PTA Catheter configuration," showing the relative dimensional interoperability of the individual "functional units" and "functional subunits" as a convenient reference. In FIG. 13, the hypothetical dimensional values for the components of the "FICS LLS PTA catheter configuration" are assigned with both "component-specific reference abbreviations" (LG, SC, PTA, DEL, and CTO) and "functional dimension-specific reference abbreviations" (TL, UL, ML, RL, BL, OL, SL, TiL). The "functional dimension-specific reference abbreviations" represent the respective lengths of the FICS components, as provided in Table 1 under Example 1. Furthermore, Table 2 provides respective formulas for calculating the "functional dimensions" corresponding to the respective components (labeled in FIG. 13; listed in Table 1), wherein the various "functional dimensions" listed in the first column of Table 2 represent the operational lengths and operational relationships among the components of the "functional units" and "functional subunits."

In FIG. 13, the functional dimension "A" refers to the constant total length TL of the FICS System, the functional dimension "B" refers to the variable usable length portion UL; the functional dimension "D" refers to the fixed total length portion of the combined total lengths of the Support Catheter SC and the Lock Grip LG; and the functional dimension "C" refers to a variably recessed length portion (describing the sheathed balloon length portion RL relative to the complete balloon length portion BL). The difference BL-RL defines the operational balloon length OL that can be variably adjusted between a minimum and maximum threshold, wherein the adjustable operational length is measured as the distance between the position of the radiopaque markers incorporated into the distal end of the balloon member of the PTA catheter and the position of the radiopaque markers incorporated into the distal end of the support catheter shaft.

TABLE 1

ABBREVIATIONS FOR FICS COMPONENTS

| | |
|---|---|
| TL | Total Length |
| UL | Usable Length |
| ML | Manifold Length |
| RL | Recessed Length |
| BL | Balloon Length |
| OL | Operational Balloon Length |
| SL | Shaft Length |
| TiL | Tip Length |
| (LG) | Lock Grip |
| (SC) | Support Catheter |
| (PTA) | PTA Catheter |
| (DIL) | Dilator |
| (CTO) | CTO Penetration Tip |

TABLE 2

CALCULATION OF FUNCTIONAL DIMENSIONS

| Functional Dimensions | EXEMPLARY CORRELATIONS | |
|---|---|---|
| A | TL (LLS) = TL (PTA) = UL (PTA) + ML (PTA) | (constant) |
| B | UL (LLS) = UL (SC) + OL (PTA) + TiL (PTA) | (variable) |
| C | D − SL (PTA) = RL (PTA) = BL (PTA) − OL (PTA) | (variable) |
| D | TL (SC) + TL (LG) = UL (SC) + ML (SC) + TL (LG) | (constant) |
| ΔB | B (max) − B (min) = OL (max) − OL (min) | (UL Range) |
| | OL (max) = BL − C (min) | |
| | OL (min) = BL − C (max) | |
| ΔC | C (max) − C (min) | (RL Range) |
| | |ΔB| = |ΔC| | |
| | Other FICS UL per (Configuration) | |
| | UL (CTO) = UL (SC) + TiL (DIL) + OL (CTO) | |
| | UL (REENTRY) = UL (SC) + TiL (Dil) + OL (REENTRY) | |

Example 2

FICS Total Length TL (A)

The "Total Length" (IL) refers to the total length of the FICS System or individual functional units. The Total Length (IL) can be derived by adding together the respective lengths of the components for the functional units and functional subunits. The relative correlations between the lengths of components for the "LLS PTA configuration" are provided in TABLE 2, as an example. Exemplary total length (TL) ranges for the respective components of the FICS System are provided in TABLE 3 (LLS PTA Configuration, UL 80 cm) and in TABLE 4 (LLS PTA Configuration, UL 135 cm) under Example 3 below. The IL of the "FICS Reentry Dilator" and/or "FICS CTO Dilator" configuration can be derived similarly (not shown). Since the TL of the "FICS LLS PTA configuration" will always exceed the TL of the "CTO Dilator" and/or "Reentry Dilator" configuration, the TL of the FICS LLS PTA configuration can be utilized by the physician for adequate GW length selection prior to commencing the procedure.

Example 3

FICS Usable Length UL (B)

The "Usable Length" (UL) refers to the indwelling/working length portion of the FICS System or the individual functional units. The UL correlates with the distance between the access point (patient entry site) and the target-treatment point that can be reached by the FICS System. The FICS System can provide a range of different, predefined ULs corresponding to the respective components of the FICS System for treating a broad range of complex lesions and/or CTOs. As examples, two usable lengths of respective components are provided for one therapeutic-specific configurations: (a) the FICS LLS PTA Configuration with a UL of 80 cm (TABLE 3); and (b) the FICS LLS PTA Configuration with a UL of 135 cm (TABLE 4). Clinically relevant access lengths correlating with the distance measurable from the most commonly used (predefined) patient entry points to a hypothetical target site (distance beyond a hypothetical lesion located in a predefined target region) are provided in TABLE 5. The usable length UL portion of the components of the FICS System can be selected based on the determined access length.

It can be shown, in absolute values, that the usable length portion "B" of the FICS system in the "LLS PTA configuration" can be adjusted in a dimensional range |ΔB| that is equivalent to the balloon extension range |ΔC|. This leads to a variable adjustability of the usable length "B" whereas the total length "A" of the FICS System can remain constant. This property differs in comparison to conventional systems, wherein both usable length and total length are constant. Due to this specific configuration, the FICS system in the "LLS PTA configuration" enables a custom length-adjustable operational balloon length that can be adapted for "lesion-length selective" dilation (optionally anchoring/centering), wherein the system itself can exhibit an adjustable UL portion substantially at the same time.

Other FICS system configurations, such as the "FICS CTO Dilator configuration" or the "FICS Reentry Dilator configuration" can exhibit variable usable length ranges, as described in TABLE 2. In the case of the FICS CTO and/or Reentry configuration, their individual operational tip lengths can be added to arrive at analogous dimensional correlations referenced in TABLE 4.

TABLE 3

FICS LLS PTA CATHETER CONFIGURATION, UL 80 cm

| all units [mm] | Min | Max | Opt |
|---|---|---|---|
| UL (SYSTEM) = UL (SC) |  | 800 |  |
| ML (SC) | 10 | 50 | 20 |
| TL (LG) | 20 | 100 | 50 |
| TiL (PTA) | 5 | 10 | 5 |
| OL (PTA) | 0 | 180 | 0-180 |
| ML (PTA) | 40 | 80 | 80 |
| TL (SYSTEM) = TL (PTA) | 875 | 1220 | 1135 |
| BL (PTA) | 10 | 200 | 200 |
| RL (PTA) | 10 | 20 | 20 |
| SL (PTA) | 820 | 930 | 850 |
| UL (PTA) | 835 | 1140 | 1055 |

TABLE 4

FICS LLS PTA CATHETER CONFIGURATION, UL 135 cm

| all units [mm] | Min | Max | Opt |
|---|---|---|---|
| UL (SYSTEM) = UL (SC) |  | 1350 |  |
| ML (SC) | 10 | 50 | 20 |
| TL (LG) | 20 | 100 | 50 |
| TiL (PTA) | 5 | 10 | 5 |
| OL (PTA) | 0 | 180 | 0-180 |
| ML (PTA) | 40 | 80 | 80 |
| TL (SYSTEM) = TL (PTA) | 1425 | 1770 | 1685 |
| BL (PTA) | 10 | 200 | 200 |
| RL (PTA) | 10 | 20 | 20 |
| SL (PTA) | 1370 | 1480 | 1400 |
| UL (PTA) | 1385 | 1690 | 1605 |

TABLE 5

ACCESS LENGTHS (across Lesion)

| | Entry Points | | | |
|---|---|---|---|---|
| all units [cm] Target Regions | CFA ipsilateral | CFA contralateral | Brachial | Radial |
| Illiac | 1-30 | 30-60 | 70-100 | 100-130 |
| SFA | 1-30 | 30-60 | 100-130 | 130-160 |
| BTK | 50-80 | 80-110 | 150-180 | 180-210 |

CFA = common femoral artery
SFA = superficial femoral artery
BTK = below the knee Example 4

FICS Compatibility with Guide Wire Length

The TL correlates with the GW length needed to effectively operate all combined functional units in their respective configurations (on/over the guide wire). When planning an interventional procedure, the physician can use the total system length as an orientation for selecting an adequately sized guide wire. TABLE 6 provides a list of recommended and calculated GW lengths correlating with the FICS total length (LLS PTA configuration).

TABLE 6

FICS GUIDEWIRE LENGTH COMPATIBILITY

| GW LENGTH COMPATIBILITY | | TOTAL LENGTH (A) | USABLE LENGTH (B) |
|---|---|---|---|
| (recommended) | (calc.)* | all units [mm] | |
| 4500 | 4370 | 2135 | 1800 |
| 4000 | 3970 | 1935 | 1600 |
| 3800 | 3770 | 1835 | 1500 |
| 3500 | 3470 | 1685 | 1350 |
| 3200 | 3170 | 1535 | 1200 |
| 2800 | 2770 | 1335 | 1000 |
| 2600 | 2570 | 1235 | 900 |
| 2400 | 2370 | 1135 | 800 |
| 2000 | 1970 | 935 | 600 |

*GW LENGTH COMPATIBILITY = [(SYSTEM TL (MAX) * 2) + 100]

Example 5

FICS GW Diameter Compatibility ("Guidewire Compatibility")

The "guide wire compatibility" refers to the minimum inner diameter (ID) of the lumen of a functional unit/ instrument for passing a guidewire of certain outer diameter without resistance. Guide wire compatibility is governed by the GW lumen ID of each insertable functional unit, for example, the (GW lumen) ID of the Dilator, the PTA catheter, or respectively the lumen ID of the hypotube coaxially embedded into the dilator tip design as utilized in the "CTO Dilator" and/or "Reentry Dilator" configuration. Guide wires can typically be offered with outer diameter ranges between 0.014-0.035 [in], equivalent to 0.356-0.889 [mm]. The functional units of the FICS, particularly the PTA catheter, dilator and hypotube component can be configured to be 0.018 in./0.457 mm compatible. Other dimensions and ranges can be contemplated for different clinical applications.

Example 6

FICS Introducer Sheath Compatibility

The term "Sheath Compatibility" refers to the maximum instrument outer diameter (OD) along the UL that can be introduced through an introducer sheath of commensurate inner diameter without resistance. The components of the FICS System can be dimensionally configured based on the relative diameters of the components. The FICs system can be designed to pass through the inner diameter of introducer sheaths having a variable range. Thus the outer diameter along the usable length portion of the FICS system can be configured to be receivable through an introducer sheath having a compatible inner diameter. For example, TABLE 7 provides the dimensions of a PTA balloon member (widths and lengths) that may be recommended for obtaining sheath compatibility suitable for the FICS LLS PTA configuration, wherein the PTA catheters having balloon diameters that can range between 2.0-7.0 mm, for example. The operational balloon length OL (Table 7) can be adjusted through the interoperation of the SC, the LG and the PTA functional units as described in FIG. 12. The balloon length BL of the Dilator and the PTA catheter can be configured within a fixed range as described in TABLES 3-4. Other dimensions and ranges can be contemplated for different clinical applications. For example, a system for retrograde pedal/tibial access can be dimensioned using a sheath compatible at 3 Fr. For the FICS CTO Dilator configuration, the proximal maximum outer diameter of a polymeric tip (e.g., refer to FIGS. 6-7, components 620/720) can correspond to the minimum inner diameter of the lumen of FICS Support Catheter, for example, ranging between 3.0-4.0 Fr.

TABLE 7

FICS SHEATH COMPATIBILITY

| Balloon Diameter [mm] | Operational Balloon Length [mm] | | | | | | | |
|---|---|---|---|---|---|---|---|---|
| | 20 | 40 | 60 | 80 | 100 | 120 | 150 | 180 |
| 2.0 | 4Fr | 4Fr | 4Fr | 4Fr | 4Fr | 4Fr | 4Fr | 4Fr |
| 2.5 | 4Fr | 4Fr | 4Fr | 4Fr | 4Fr | 4Fr | 4Fr | 4Fr |
| 3.0 | 4Fr | 4Fr | 4Fr | 4Fr | 4Fr | 4Fr | 4Fr | 4Fr |
| 3.5 | 4Fr | 4Fr | 4Fr | 4Fr | 4Fr | 4Fr | 4Fr | 4Fr |
| 4.0 | 5Fr | 5Fr | 5Fr | 5Fr | 5Fr | 5Fr | 5Fr | 5Fr |
| 5.0 | 5Fr | 5Fr | 5Fr | 5Fr | 5Fr | 5Fr | 5Fr | 5Fr |
| 6.0 | 5Fr | 5Fr | 5Fr | 5Fr | 5Fr | 5Fr | 5Fr | 5Fr |
| 7.0 | 5Fr | 5Fr | 5Fr | 5Fr | 5Fr | 5Fr | 5Fr | 5Fr |

Note:
1 [Fr] = 0.333 [mm]

The foregoing description, for purposes of explanation, refers to specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and practical applications, to thereby enable others skilled in the art to best utilize the invention and various embodiments with various modifications as suitable for the particular uses contemplated. It is intended that the scope of the invention be defined by the following claims and their equivalent.

We claim:

1. A catheter system comprising:
multiple shaft-based components, including
one or more support catheters that each includes a shaft member with a central lumen, a manifold that provides fluid communication to the central lumen, and a connector,
one or more dilators that each includes a tip, a shaft member with one or more lumens, a manifold that provides fluid communication to one or more of the one or more lumens, and a connector, the dilator shaft member having an external diameter that allows the dilator shaft member to be inserted into the central lumen of the support catheter, and
one or more percutaneous transluminal angioplasty ("PTA") catheters that each includes an inflatable member attached to a shaft member with two or more lumens, a manifold that provides fluid communication to one or more of the two or more lumens, and a connector, the PTA-catheter shaft member having an external diameter that allows the PTA-catheter shaft member to be inserted into the central lumen of the support catheter; and
a lock-grip handle that includes a second connector that is complementary to the support-catheter connector, the dilator connector, and the PTA-catheter connector, a lock-grip body, and a first connector complementary to the second connector, the lock-grip handle providing a seal to inhibit fluid communication to an enclosed volume between an inner surface of a lumen of a first shaft-based component, selected from the multiple shaft-based components, connected to the second connector and an external surface of a second shaft-based component, selected from the multiple shaft-based components, inserted through the first connector and into the lumen of the first shaft-based component.

2. The catheter system of claim 1 wherein the first and second shaft-based components and the lock-grip handle are assembled to form multiple different multi-component catheters, including:
a first multi-component catheter, wherein the first shaft-based component is a support catheter selected from the one or more support catheters and wherein the second shaft-based component is a dilator selected from the one or more dilators;
a second multi-component catheter, wherein the first shaft-based component is a support catheter selected from the one or more support catheters and wherein the second shaft-based component is a PTA catheter selected from the one or more PTA catheters; and
a third multi-component catheter, wherein a third shaft-based component, selected from the multiple shaft-based components, is a support catheter selected from the one or more support catheters connected to a valve into which the shaft of the first shaft-based component, which is a PTA catheter selected from the one or more PTA catheters, is inserted in order to extend into the central lumen of the third shaft-based component, and wherein the second shaft-based component is a dilator selected from the one or more dilators.

3. The catheter system of claim 1 wherein the one or more support catheters of the multiple shaft-based components include at least one support catheter with a support-catheter shaft member having a first end and a second end, the first end connected to a second end of the support-catheter manifold, and the second end having a circular edge, the plane of which is orthogonal to a long axis of the central lumen.

4. The catheter system of claim 3 wherein the support-catheter connector comprises a female luer lock mounted at a first end of the support-catheter manifold.

5. The catheter system of claim 3 wherein the support-catheter manifold includes one or more flushing ports through which fluids are introduced into the central lumen.

6. The catheter system of claim 3 wherein the support-catheter shaft member includes one or more radiopaque markers.

7. The catheter system of claim 1 wherein the one or more dilators of the multiple shaft-based components include at least one dilator with a dilator shaft member having a first end and a second end, the first dilator-shaft-member end connected to a second end of the dilator manifold and the second dilator-shaft-member end containing one of:
a portion of a non-inflatable dilator tip;
a portion of an inflatable dilator tip; and
a portion of an inner tubular member.

8. The catheter system of claim 7 wherein the portion of the non-inflatable dilator tip is positioned within a single lumen within the dilator shaft member.

9. The catheter system of claim 7 wherein the portion of the inflatable dilator tip is positioned within a first lumen within the dilator shaft member and connected to a second, inflation lumen.

10. The catheter system of claim 7 wherein the inner tubular member contains a portion of a dilator tip.

11. The catheter system of claim 7 wherein the dilator connector comprises a female luer lock mounted at a first end of the dilator manifold.

12. The catheter system of claim 7 wherein the dilator shaft member includes one or more radiopaque markers.

13. The catheter system of claim 1 wherein the one or more PTA catheters of the multiple shaft-based components include at least one PTA catheter with a PTA-catheter shaft member having a first end and a second end, the first PTA catheter-shaft-member end connected to a second end of the PTA-catheter manifold, and the second PTA-catheter-shaft-member end connected to the inflatable member so that, when the PTA-catheter shaft member lies within the central lumen of a support catheter selected from the one or more support catheters, a length of the inflatable member that lies beyond an end of the support-catheter central lumen is varied by translating the PTA-catheter shaft-member with respect to the support-catheter shaft member.

14. The catheter system of claim 13 wherein the PTA-catheter shaft member includes one or more radiopaque markers.

15. The catheter system of claim 1 wherein the lock-grip handle provides mechanical features, that, when manipulated,
fix the relative positions of the first shaft-based component connected to the second lock-grip-handle connector and the second shaft-based component inserted through the first lock-grip-handle connector and into a lumen of the first shaft-based component;
unfix the relative positions of the first shaft-based component connected to the second lock-grip-handle connector and the second shaft-based component inserted through the first lock-grip-handle connector and into a lumen of the first shaft-based component; and
controllably advance and retract the second shaft-based component, inserted through the first lock-grip-handle connector and into a lumen of the first shaft-based component connected to the second lock-grip-handle connector, with respect to the first shaft-based component.

16. A catheter system comprising:
multiple shaft-based components, including
one or more support catheters, each including a connector,
one or more dilators, each including a connector, and
one or more percutaneous transluminal angioplasty ("PTA") catheters, each including a connector; and
a lock-grip handle that includes
a second connector complementary to the support-catheter connector, the dilator connector, and the PTA-catheter connector,
a first connector complementary to the second connector,
a lock-grip body,
a seal to inhibit fluid communication to an enclosed volume between an inner surface of a lumen of a first shaft-based component, selected from the multiple shaft-based components, connected to the second connector and an external surface of a second shaft-based component, selected from the multiple shaft-based components, inserted through the first connector and into a lumen of the first shaft-based component, and
features that, when manipulated,
fix the relative positions of the first shaft-based component connected to the second lock-grip-handle connector and the second shaft-based component inserted through the first lock-grip-handle connector and into a lumen of the first shaft-based component;
unfix the relative positions of the first shaft-based component connected to the second lock-grip-handle connector and the second shaft-based component inserted through the first lock-grip-handle connector and into a lumen of the first shaft-based component; and
controllably advance and retract the second shaft-based component, inserted through the first lock-grip-handle connector and into a lumen of the first shaft-based component connected to the second lock-grip-handle connector, with respect to the first shaft-based component.

17. The catheter system of claim 16 wherein the lock-grip-handle body further comprises:
a pushing handle that includes
a first pushing-handle member that includes the first lock-grip-handle connector at a first end and a female-threaded cylindrical member at a second end, the lock-grip-handle seal, and
a second pushing-handle member that includes a cylindrical male-threaded member at a first end that is complementary to the female-threaded cylindrical member of the first pushing-handle member and a cylindrical engagement member at a second end;

a cam assembly that includes
- a first cylindrical cam, into a first end of which the cylindrical engagement member of the first pushing-handle member is inserted and which includes a first cylindrical cam feature at a second end, and
- a second cylindrical cam with a second cylindrical cam feature at a first end that is complementary to the first cylindrical cam feature;

a spring; and a cylindrical casing that contains the cam assembly and the spring.

18. The catheter system of claim 17 wherein, when the first pushing-handle member and second pushing-handle member are rotated to thread the female-threaded cylindrical member further onto the male-threaded cylindrical member, the seal is compressed to lock relative positions of the first shaft-based component connected to the second lock-grip-handle connector and the second shaft-based component inserted through the first lock-grip-handle connector and into a lumen of the first shaft-based component.

19. The catheter system of claim 17 wherein, when the pushing-handle has locked relative positions of the first shaft-based component connected to the second lock-grip-handle connector and the second shaft-based component inserted through the first lock-grip-handle connector and into a lumen of the first shaft-based component and when the pushing handle is pushed forward with respect to the first shaft-based component, the second shaft-based component is advanced forward relative to the first shaft-based component.

20. The catheter system of claim 17 wherein rotation of the pushing-handle imparts a rotation to a tip inserted into the shaft of the second shaft-based component inserted through the first lock-grip-handle connector and into a lumen of the first shaft-based component connected to the second lock-grip-handle connector.

* * * * *